United States Patent [19]
Yaghi

[11] Patent Number: 5,648,508
[45] Date of Patent: Jul. 15, 1997

[54] CRYSTALLINE METAL-ORGANIC MICROPOROUS MATERIALS

[75] Inventor: Omar M. Yaghi, Phoenix, Ariz.

[73] Assignee: Nalco Chemical Company, Naperville, Ill.

[21] Appl. No.: 560,224

[22] Filed: Nov. 22, 1995

[51] Int. Cl.$^6$ .............................. C07F 9/00; C07F 13/00; C07F 5/00

[52] U.S. Cl. .................. 556/9; 556/10; 556/13; 556/19; 556/28; 556/30; 556/44; 556/49; 556/55; 556/61; 556/78; 556/106; 556/115; 556/136; 556/132; 556/147; 556/1; 534/16

[58] Field of Search ................... 556/132, 9, 10, 556/13, 19, 28, 30, 44, 49, 55, 61, 78, 106, 115, 136, 147; 534/16

[56] References Cited

PUBLICATIONS

"T-Shaped Molecular Building Units in the Porous Structure of Ag(4,4'-bpy). $NO_3$" O.M. Yaghi and H. Li, *J. Am. Chem Soc.* 1996, 118, 295-296.

"Selective Binding and Removal of Guests in a Microporous Metal-Organic Framework," O. M. Yaghi, G. Li, and H. Li, *Nature*, 1995, 378, 703-706.

"Hydrothermal Synthesis of a Metal-Organic Framework Containing Large Rectangular Channels", O.M. Yaghi & H. Li, *J. Am. Chem. Soc.* 1995, 117, 10401-02.

"Open-Framework Solids with Diamond-Like Structures Prepared from Clusters and Metal-Organic Building Blocks," O.M. Yaghi, D.A. Richardson, G. Li, C.E. Davis, T.K. Groy, *Mater. Res. Soc. Symp. Proc.*, 1995, 371–15–19.

"Preparation of Single Crystals of Coordination Solids in Silica Gels: Synthesis & Structure of $Cu(1,4-C_4H_4N_2)$ $(C_4O_4)$ $(OH_2)_4$" O.M. Yaghi, Guangming Li, and T.L. Groy, *J. Solid State Chem.*, 1995, 117, 256–260.

"Mutually Interpenetrating Sheets and Channels in the Extended Structure of [Cu(4,4'-bpy)Cl]**", O.M. Yaghi, Guangming Li, *Angew. Chem. Int. Ed. Engl.*, 1995, 34, 207–209.

"Conversion of Hydrogen-Bonded Managanese (||) and Zinc (||) Squarate ($C_4O_4^{2-}$) Molecules, Chains, and Sheets to Three-dimensional Cage Networks," O.M. Yaghi, Guangming Li, T.L. Croy, *J. Chem. Soc., Dalton Trans.*, 1995, 727–732.

"Directed Transformation of Molecules to solids: Synthesis of a Microporous Sulfide from Molecular Germanium Sulfide Cages" O.M. Yaghi, Z. Sun, D. A. Richardson, R.L. Groy, *J. Am. Chem. Soc.*, 1994, 116, 807–808.

"Rhenium–Selenium–Chlorine Solid Phases: Cluster Excision and Core Substitution Reactions of Molecular Species", O.M. Yaghi, M.J. Scott, R.H. Holm, *Inorg. Chem.* 1992, 31, 4778–4784.

"New Directions in Polyoxovanadate Chemistry: From Cages and Clusters to Baskets, Belts, Balls, and Barrels", W.G. Klemperer, T.A. Marquart, O.M. Yaghi, *Angew. Chem., Int. Ed. Engl.* 1992, 31, 49–51.

"Mono–and Dipotonation of the $[\eta^5-C_5H_5)TiW_5O_{18})]^{3-}$ and $[\eta^5-C_5Me_5)TiW_5O_{18})]^{3-}$ Anions", T.M. Che, v.W. Day, L.C. Francesconi, W.G. Klemperer, D.J. Main, A. Yagasaki, O.M. Yaghi, *Inorg. Chem.* 1992, 31, 2920–2928.

"Shape–Selective Binding of Nitriles to the Inorganic Cavitand, $V_{12}O_{32}^{4-}$", W.G. Klemperer, T.A. Marquart & O.M. Yaghi, *Mat. Chem. Phys.* 1991, 29, 97–104.

"Potassium Octadecatungstodiphosphates (V) and Related Lacunary Compounds", W.G. Klemperer, O.M. Yaghi in *Inorg. Synth.*, A.P. Ginsberg, ed., Wiley: N.Y. 1990, 27, 105–111.

"A New Structure Type in Polyoxoanion Chemistry: Synthesis and Structure of the $V_5O_{14}^{3-}$ Anion", V. W. Day, W.G. Klemperer, O.M. Yaghi, *J. Am. Chem. Soc.* 1989, 111, 4518–4519.

"Synthesis and Characterization of a Soluble Oxide Inclusion Complex, $[CH_3CN \subset (V_{12}O_{32})^{4-0}]$", V.W. Day, W. G. Klemperer, O.M. Yaghi, *J. Am. Chem. Soc.* 1989, 111, 5959–5961.

"Selective Oxidation Chemistry of soluble Oxides: A Progress Report", V.W. Day, W.G. Klemperer, S.P. Lockledge, D.J. Main, F.S. Rosenberg, , R.C. Wang, O.M. Yaghi in *Metal–Metal Bonds And Clusters in Chemistry And Catalysis*, J.P. Fackler, ed., Plenum: N.Y., 1989, 161–170.

*Primary Examiner*—Porfirio Nazario-Gonzalez
*Attorney, Agent, or Firm*—Robert A. Miller; James J. Drake

[57] ABSTRACT

Novel metal-organic microporous materials are prepared in solution using mild reaction conditions from a metal or metalloid ion with a ligand containing multidentate functional groups in the presence of a templating agent. The resultant microporous materials are useful in the purification of liquids and gases.

61 Claims, 4 Drawing Sheets

CRYSTALLINE METAL-ORGANIC MICROPOROUS MATERIALS

INTRODUCTION

This invention is directed to the composition, method of preparation, and uses of new, novel crystalline microporous solids which are prepared in a solution reaction by admixing certain metal salts with an organic ligand containing multidentate functional groups or a mixture of organic ligands containing multidentate and monodentate functional groups in the presence of a templating agent. The materials may also be prepared in a viscous matrix whereby large crystals of the microporous solid can be advantageously prepared. Optionally, the materials may be advantageously prepared to contain voids by removing template materials after preparation. The resultant microporous materials are useful for the adsorption of molecules or ions of impurities from liquids and gases. Through the careful selection of metal ion, ligand, and templating agent, rigid and stable microporous materials can be prepared having desired pore size openings useful for particular tasks.

BACKGROUND OF THE INVENTION

The utility of microporous solids such as the zeolite-type aluminosilicates, aluminophosphates, and their metal substituted derivatives is well established in industrial processes involving ion-exchange, separation, and catalysis (U.S. Pat. Nos. 4,310,440, 4,440,871, and 4,500,651). The widespread application of these so called zeolitic materials is due to their ability to include molecules and ions in a selective and reversible fashion, a property conferred by the stability and rigidity of their porous frameworks.

Although most of these frameworks are based on the oxide of the metal, a recent invention showed that similar materials can be produced from the sulfide and selenide of the metal (U.S. Pat. No. 4,880,761).

While the syntheses of oxide zeolites and their sulfide and selenide analogues are well known, the capability of rationally designing the shape, size, and function of the pores of zeolites or microporous materials is lacking. In particular, the method for zeolite synthesis requires the mixing of an alkali metal hydroxide with aqueous solutions of silicate and aluminate anions to form a hydrated aluminosilicate gel of complex composition. Zeolitic solids are obtained by the subsequent heating of the gel (up to 200° C.) under water vapor pressure conditions in a closed vessel. The complexity of the gel precludes any possibility of controlling the structural organization of the zeolitic solid. Thus, zeolite synthesis has remained as much an art as a science (See A. Dyer, "An Introduction to Zeolite Molecular Sieves" John Wiley and Sons, New York (1988); R. M. Barrer, "Hydrothermal Chemistry of Zeolites" Academic Press, New York (1982); J. M. Newsam, "The Zeolite Cage Structure", Science, 231:1093 (1986)).

An extensive amount of work has been done on the synthesis of metal-organic solids, though none of the resulting materials possess microporous properties comparable to those obtained through the use of this invention.

For example, Toshitake Iwamoto, "Inclusion Compounds of Multi-Dimensional Cyanometal Complex Hosts" *Inclusion Compounds*, Vol. 5 (Eds.: J. L. Atwood, J. E. D. Davies, D. D. Macnicol), Oxford University Press (1991) p. 177, and references therein, provides a review on the Hoffmann-type compounds and their derivatives, where 1D, 2D and 3D frameworks are produced by linking one metal atom M to another M' to form M—CN—M' type solids. Other reports are B. F. Hoskins and R. Robson, "Design and Construction of a New Class of Scaffolding-Like Materials Comprising Infinite Polymeric Frameworks of 3D-Linked Molecular Rods. A Reappraisal of the $Zn(CN)_2$ and $Cd(CN)_2$ Structures and the Synthesis and Structure of the Diamond-Related Frameworks $[N(CH_3)_4][Cu^IZn^{II}(CN)_4]$ and $Cu^I[4,4',4'',4'''$-tetracyanotetraphenylmethane]-$BF_4 \cdot xC_6H_5NO_2$," *J. Am. Chem. Soc.*, 112:1546 (1990); B. F. Hoskins and R. Robson, "Infinite Polymeric Frameworks Consisting of Three-Dimensionally Linked Rod-Like Segments," *J. Am. Chem. Soc.* 111:5962 (1989); S. R. Batten, B. F. Hoskins, and R. Robson, "3D Knitting Patterns. Two Independent, Interpenetrating Rutile-Related Infinite Frameworks in the Structure of $Zn[C(CN)_3]_2$," *J. Chem. Soc., Chem. Commun.* 445 (1991); B. F. Abrahams, B. F. Hoskins, D. M. Michall, and R. Robson, "Assembly of Porphyrin Building Blocks into Network Structures with Large Channels," *Nature* 369:727 (1994); G. B. Gardner, D. Venkataraman, J. S. Moore, and S. Lee, "Spontaneous Assembly of a Hinged Coordination Network," *Nature* 374:792 (1995); 0. M. Yaghi, G. Li, and T. L. Groy, "Preparation of Single Crystals of Coordination Solids in Silica Gels: Synthesis and Structure of $Cu^{II}(1,4-C_4H_4N_2)(C_4O_4)(OH_2)_4$," *J. Solid State Chem.*, 256 (1995). 0. M. Yaghi and G. Li, "Presence of Mutually Interpenetrating Sheets and Channels in the Extended Structure of $Cu(4,4'$-bipyridine$)Cl$," *Angew. Chem., Int. Ed. Engl.*, 207 (1995).

All metal-organic solids prepared to date are either (a) one dimensional (1D), two dimensional (2D), or three dimensional (3D) dense solids having no porosity or (b) solids that are made by the formation of linkages between the metal, M, and a bifunctional, trifunctional, or tetrafunctional organic ligand, L, containing monodentate functional groups, around a templating agent, T. One possible structure, having a diamond-like framework, is shown as an example of the effect of the templating agent (Formula 1).

Formula 1 below represents a schematic illustration of the assembly of a metal-organic framework in the presence of a templating agent, T. Here a fragment of a solid is shown with the small spheres representing a metal ion, M, capable of binding to four ligands in a tetrahedral geometry, while the dark rod represents a bifunctional organic ligand, L, capable of binding metal ions at its ends and encapsulating the templating agent within a pore.

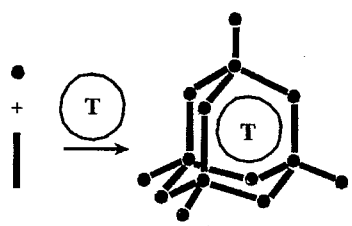

Formula 1

Metal-organic solids may assume other framework types, depending on the preferred coordination geometry of the metal ion and the organic ligand.

Microporosity in the aforementioned metal-organic solids has not been demonstrated due to at least two problems. First, the templating agent interacts strongly with the metal-organic framework, thus making it impossible to remove the templating agent from the solid without altering or destroying the framework. In that way, the ability of the solid to adsorb another molecule, or readsorb the templating agent to yield the original material, is lost. So, it is desirable to keep the templating agent-framework interactions to a minimum while maximizing the strength of intra-framework bonding between the organic ligand and the metal ion. Secondly, for many metal-organic solids the pores are not occupied by templating agents, but with interpenetrated frameworks. Formula 2 below shows an example where one framework has interpenetrated another identical framework. Extensive framework interpenetration can cause the porous space of a single framework to be filled, resulting in a dense solid that will not adsorb molecules or ions. In Formula 2 below, two interpenetrated diamond-like frameworks (distinguished with light and dark shades) are shown. Each framework standing alone forms a porous structure. However, interpenetration in this case fills those pores.

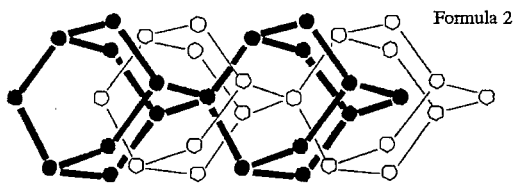

Formula 2

For a given solid, as the number of interpenetrating frameworks increases, the material becomes more densly packed, and thus, the channels and pores present in the material become smaller, perhaps to the extent that the material loses porosity to even the smallest adsorbing species. Attempts to rationally design microporous materials have resulted in nonporous solids due to interpenetration (see O. Ermer and L. Lindenberg, "Double-Diamond Inclusion Compounds of 2,6-Dimethylideneadamantane- 1,3,5,7-tetracarboxylic Acid" *Helv. Chim. Acta* 74:825 ( 1991 ); O. Ermer, "Five-Fold Diamond Structure of Adamantane-1,3,5,7-tetracarboxylic Acid" *J. Am. Chem. Soc.* 110:3747 (1988); S. R. Batten, B. F. Hoskins, and R. Robson, "3D Knitting Patterns. Two Independent, Interpenetrating Rutile-Related Infinite Frameworks in the Structure of Zn[C(CN)$_3$]$_2$," *J. Chem. Soc., Chem. Commun.* 445 (1991)).

Therefore, this invention details the first successful rational synthetic approach to the formation of crystalline metal-organic solids that show effective microporous activity, having (a) structural integrity preserved in the absence of a templating agent and (b) no or minimal amounts of interpenetrating frameworks so that channels and pores that can accomodate transfer and binding of molecules or ions exist within the solid. Given the great impact of zeolitic materials on the global economy, it would be a significant improvement in the art if a method existed for rationally designing crystalline microporous materials.

The method of this invention provides to the art such a process. By the use of the subject invention, crystalline microporous materials can be prepared which have controlled pore distributions and sizes, and which are useful in a variety of industries.

These materials form by the solution reaction of a metal ion selected from the group consisting of: Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, and Bi, with a ligand having multidentate functional groups, and a templating agent.

It is believed that the invention of the present application provides to the art a novel method for the preparation of microporous materials which are useful in industries such as catalysis, gas purification, ion-exchange, the removal of impurities from industrial aqueous streams, the removal of impurities from hydrocarbon streams, the removal of color from paper mill waste waters, the removal of metals from aqueous solutions, the removal of metals from hydrocarbon solutions, the removal of hydrocarbon contaminants from aqueous systems, the removal of hydrocarbon contaminants from hydrocarbon systems, filtration, and seperation materials, and the like.

It is accordingly an object of this invention to provide to the art a method for the preparation of novel microporous materials. It is a still further object of this invention to provide to the art a method for the preparation of novel microporous materials in a simple straightforward manner which method would allow control over the resultant final product.

It would be a further improvement in the art if the synthesis of microporous materials could be performed under room temperature or mild reaction conditions (relative to those used to synthesize oxide microporous materials). It would be a still further improvement in the art if the microporous materials could be prepared from simple metal salts and organic ligands. It would be an even further improvement in the art if the aforementioned synthetic method could result in the formation of crystalline microporous materials, having no pore or channel inhomogeneity.

Further objects of this invention will appear hereinafter.

BRIEF DESCRIPTION OF THE DRAWINGS

FIGS. 1–4 will be more fully explained in the examples contained herein.

THE INVENTION

Figure 1:
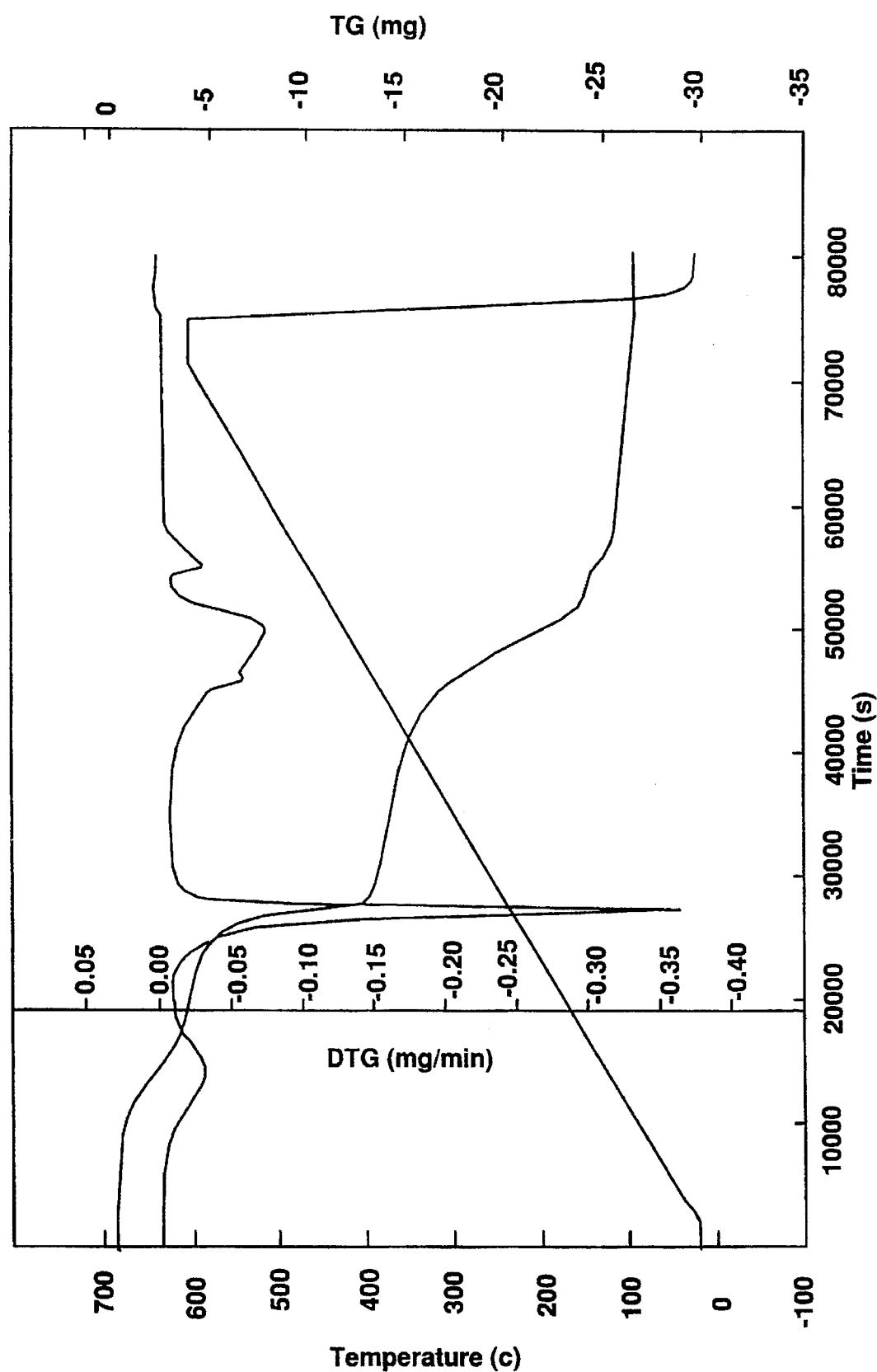
FIG. 1 is a thermal gravametric analysis trace of CoC$_6$H$_3$(COOH$_{1/3}$)$_3$(NC$_5$H$_5$)$_2$.2/3 NC$_5$H$_5$.

The basic process of the invention used for the preparation of the crystalline or microcrystalline microporous materials of this invention comprises the step of admixing:

A. a solution containing one or more metal salts containing metal ions from the group consisting of:

Mg$^{2+}$, Ca$^{2+}$, Sr$^{2+}$, Ba$^{2+}$, Sc$^{3+}$, Y$^{3+}$, Ti$^{4+}$, Zr$^{4+}$, Hf$^{4+}$, V$^{4+}$, V$^{3+}$, V$^{2+}$, Nb$^{3+}$, Ta$^{3+}$, Cr$^{3+}$, Mo$^{3+}$, W$^{3+}$, Mn$^{3+}$, Mn$^{2+}$, Re$^{3+}$, Re$^{2+}$, Fe$^{3+}$, Fe$^{2+}$, Ru$^{3+}$, Ru$^{2+}$, Os$^{3+}$, Os$^{2+}$, Co$^{3+}$, Co$^{2+}$, Rh$^{2+}$, Rh$^+$, Ir$^{2+}$, Ir$^+$, Ni$^{2+}$, Ni$^+$, Pd$^{2+}$, Pd$^+$, Pt$^{2+}$, Pt$^+$, Cu$^{2+}$, Cu$^+$, Ag$^+$, Au$^+$, Zn$^{2+}$, Cd$^{2+}$, Hg$^{2+}$, Al$^{3+}$, Ga$^{3+}$, In$^{3+}$, Tl$^{3+}$, Si$^{4+}$, Si$^{2+}$, Ge$^{4+}$, Ge$^{2+}$, Sn$^{4+}$, Sn$^{2+}$, Pb$^{4+}$, Pb$^{2+}$, As$^{5+}$, As$^{3+}$, As$^+$, Sb$^{5+}$, Sb$^{3+}$, Sb$^+$, and Bi$^{5+}$, Bi$^{3+}$, Bi$^+$; along with the corresponding metal salt counteranion with, B. one or more ligands, said ligands having at least one of:

i. an alkyl group substructure, having from 1 to 10 carbon atoms;

ii. an aryl group substructure, having from 1 to 5 phenyl rings;

iii. an alkyl or aryl amine substructure, consisting of alkyl groups having from 1 to 10 carbon atoms or aryl groups having from 1 to 5 phenyl rings; said ligand having bound thereto at least one multidentate functional group "X", which is covalently bound to the substructure of the ligand, and wherein X is selected from the group consisting of: CO$_2$H, CS$_2$H, NO$_2$, SO$_3$H, Si(OH)$_3$, Ge(OH)$_3$, Sn(OH)$_3$, Si(SH)$_4$, Ge(SH)$_4$, Sn(SH)$_4$, PO$_3$H, AsO$_3$H, AsO$_4$H, P(SH)$_3$, As(SH)$_3$; CH(RSH)$_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings; and, $CH(SH)_2$, $C(SH)_3$, $CH(NH_2)_2$, $C(NH_2)_3$, $CH(OH)_2$, $C(OH)_3$, $CH(CN)_2$, and $C(CN)_3$;

in the presence of;

C. a templating agent, selected from the group consisting of:

a. alkyl amines and their corresponding alkyl ammonium salts, containing linear, branched, or cyclic aliphatic groups, having from 1 to 20 carbon atoms (and their corresponding ammonium salts);

b. aryl amines and their corresponding aryl ammonium salts having from 1 to 5 phenyl rings;

c. alkyl phosphonium salts, containing linear, branched, or cyclic aliphatic groups, having from 1 to 20 carbon atoms;

d. aryl phosphonium salts, having from 1 to 5 phenyl rings;

e. alkyl organic acids and the corresponding alkyl organic anions (and salts) containing linear, branched, or cyclic aliphatic groups, having from 1 to 20 carbon atoms;

f. aryl organic acids and their corresponding aryl organic anions and salts, having from 1 to 5 phenyl rings;

g. aliphatic alcohols, containings linear, branched, or cyclic aliphatic groups, having from 1 to 20 carbon atoms;

h. aryl alcohols having from 1 to 5 phenyl rings;

i. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of the aforementioned inorganic anions, j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, and trifluoromethylsulfonic acid.

The invention described herein addresses the above by teaching a method for the synthesis of crystalline microporous materials by the appropriate combination of solutions of a metal salt(s), an organic ligand(s), and a templating agent, to give structurally stable and rigid materials having a desired pore shape, size, and function.

Microporous materials hereunder can be obtained only by the appropriate choice of metal ion, organic ligand(s), and templating agent.

The synthesis of the microporous materials described in this invention utilizes not only desirable properties (symmetry, rigidity, and functionality) of organic ligands and metal ions, but also it employs ligands that possess multidentate functional groups, which impart stability and rigidity to the resulting microporous metal-organic solids, while inhibiting the interpenetration of frameworks.

The Ligands

For the purposes of this invention, a multidentate functional group is defined as a moiety bound to an organic ligand or amine ligand substructure, L, and in which the moiety has the potential to have at least two atoms, X, from the general formula, $A(RX)_2$, either (a) bound to a single metal ion, or (b) bound to two metal ions. A specific example of a multidentate functional group having the $A(RX)_2$ formula is $CH(CH_2OH)_2$, where A=CH, R=$CH_2$, and X=O, as shown in Formulas 3a and 3b below:

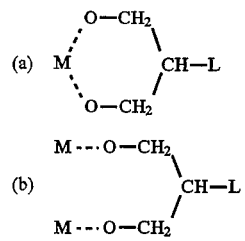

Formula 3

A multidentate functional group according to the above definition can also be represented by the formula $AX_2$. A specific example of a multidentate functional group having the $AX_2$ formula is the carboxylate anion, $CO_2^-$. The carboxylate anion has the potential to bind to a metal ion in either a bidentate (a) or monodentate (b) fashion, as shown in Formula 4. It is not a requirement of this invention that multidentate functional groups

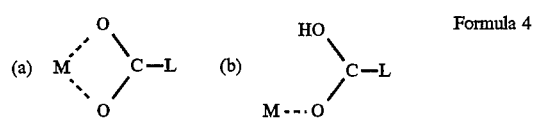

Formula 4 always bind in a multidentate fashion to afford stable microporous materials. Rather, this invention teaches that the use of ligands that contain multidentate functional groups affords rigid and stable metal-organic microporous materials.

For the purposes of this invention, an organic ligand or amine ligand substructure is defined as being an alkyl or cycloalkyl group, consisting of 1 to 20 carbon atoms, an aryl group, consisting of 1 to 5 phenyl rings, or an alkyl or aryl amine, consisting of alkyl or cycloalkyl groups having from I to 20 carbon atoms or aryl groups consisting of 1 to 5 phenyl rings, and in which multidentate functional groups are covalently bound to the substructure of the ligand. Some examples of organic ligand or amine ligand substructures are given in Formula 5 below:

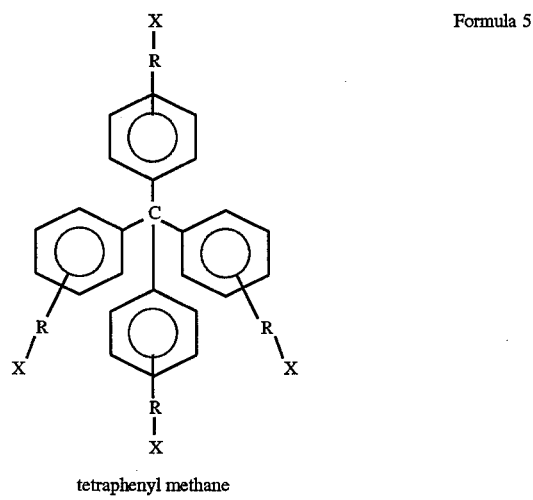

Formula 5 tetraphenyl methane

-continued

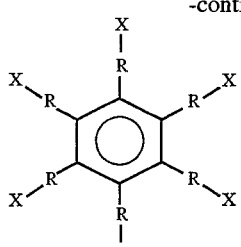
phenyl

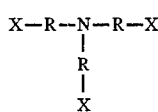
alkyl or aryl amine

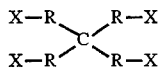
methane

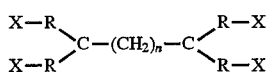
alkane

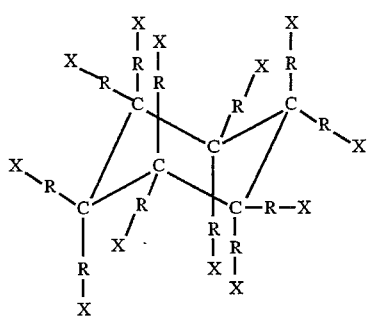
cyclohexane

-continued

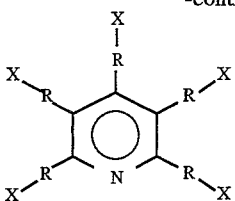
pyridine

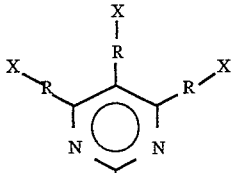
di-pyrazine

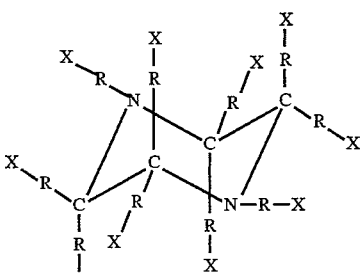
piperazine where X is a multidentate functionality selected from the group consisting of $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings; and, $CH(SH)_2$, $C(SH)_3$, $CH(NH_2)_2$, $C(NH_2)_3$, $CH(OH)_2$, $C(OH)_3$, $CH(CN)_2$, and $C(CN)_3$.

This invention further teaches that the cycloalkyl or aryl substructure may consist of 1 to 5 rings that consist either of all carbon or a mixture of carbon, with nitrogen, oxygen, sulfur, boron, phosphorous, silicon and aluminum atoms making up the ring. Some examples of such substructures are given in Formula 6 below:

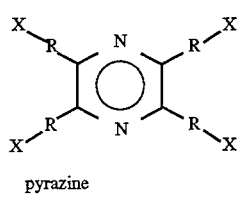
pyrazine

Formula 6

Preferred ligands of the invention are those that contain carboxylic acid functional groups. A preferred ligand of the invention is 1,3,5-benzenetricarboxylic acid (BTC), also called trimesic acid (Formula 8a). Examples given later in this invention detail how this trifunctional bidentate ligand has been used to synthesize rigid and stable metal-organic microporous materials using the metal ions cobalt(II) and zinc(II).

Another aspect of this invention teaches that crystalline metal-organic microporous materials can be synthesized by the addition of a solution of a metal salt to a solution containing an appropriate blend of ligands, some of which contain multidentate functional groups, as defined previously, and others of which contain monodentate functional groups, in the presence of a suitable templating agent.

For the purposes of this invention, a monodentate functional group is defined as a moiety bound to an organic ligand or amine ligand substructure, L, as defined previously, which can form only one bond to a metal ion. According to this definition, a ligand may contain one or more monodentate functional groups. For example, cyclohexylamine and 4,4'-bipyridine are ligands that contain monodentate functional groups, as shown in Formula 7, since each functional group is capable of binding to only one metal ion.

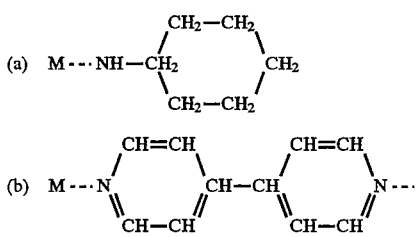

Formula 7

According to this definition, cyclohexylamine is a monofunctional ligand containing a monodentate functional group and 4,4'-bipyridine is a difunctional ligand containing two monodentate functional groups. Specific examples of ligands containing monodentate functional groups are pyridine, which is a monofunctional ligand, hydroquinone, which is a difunctional ligand, and 1,3,5-tricyanobenzene, which is a trifunctional ligand.

Examples of ligands having monodentate functional groups that can be blended with ligands that contain multidentate functional groups to make microporous materials in the presence of a suitable metal ion and a suitable templating agent are:

A. Amines that contain alkyl or cycloalkyl groups, containing from 1 to 20 carbon atoms, or aryl groups, containing from 1 to 5 phenyl rings. Examples of monofuntional amines are methylamine, ethylamine, n-propylamine, iso-propylamine, n-butylamine, sec-butylamine, iso-butylamine, tert-butylamine, n-pentylamine, neo-pentylamine, n-hexylamine, pyrrolidine, 3-pyrroline, piperidine, cyclohexylamine, morpholine, pyridine, pyrrole, aniline, quinoline, isoquinoline, 1-azaphenanthrene, and 8-azaphenanthrene. Examples of difunctional and trifunctional amines are 1,4-diaminocyclohexane, 1,4-diaminobenzene, 4,4'-bipyridyl, imidazole, pyrazine, 1,3,5-triaminocyclohexane, 1,3,5-triazine, and 1,3,5-triaminobenzene.

B. Alcohols that contain alkyl or cycloalkyl groups, containing from 1 to 20 carbon atoms, or aryl groups, containing from 1 to 5 phenyl rings. Examples of monofuntional alcohols are methanol, ethanol, n-propanol, iso-propanol, allyl alcohol, n-butanol, iso-butanol, sec-butanol, tert-butanol, n-pentanol, iso-pentanol, sec-pentanol, neo-pentanol, n-hexanol, cyclohexanol, phenol, benzyl alcohol, and 2-phenylethanol. Examples of difunctional and trifunctional alcohols are 1,4-dihydroxycyclohexane, hydroquinone, catechol, resorcinol, 1,3,5-trihydroxybenzene, and 1,3,5-trihydroxycyclohexane.

C. Ethers that contain alkyl or cycloalkyl groups, containing from 1 to 20 carbon atoms, or aryl groups, containing from 1 to 5 phenyl rings. Examples of ethers are diethyl ether, furan, and morpholine.

D. Thiols that contain alkyl or cycloalkyl groups, containing from 1 to 20 carbon atoms, or aryl groups, containing from 1 to 5 phenyl rings. Examples of monofuntional thiols are thiomethane, thioethane, thiopropane, thiocyclohexane, thiophene, benzothiophene, and thiobenzene. Examples of difunctional and trifunctional thiols are 1,4-dithiocyclohexane, 1,4-dithiobertzene, 1,3,5-trithiocyclohexane, and 1,3,5-trithiobenzene.

E. Nitriles that contain alkyl or cycloalkyl groups, containing from 1 to 20 carbon atoms, or aryl groups, containing from 1 to 5 phenyl rings. Examples of monofuntional nitriles are acetonitrile, propanenitrile, butanenitrile, n-valeronitrile, benzonitrile, and p-tolunitrile. Examples of difunctional and trifunctional nitriles are 1,4-dinitrilocyclohexane, 1,4-dinitrilobenzene, 1,3,5-trinitrilocyclohexane, and 1,3,5-trinitrilobenzene.

F. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, thiocyanide and isonitrile, and the corresponding acids and salts of the aforementioned inorganic anions.

Formula 8 gives a specific example in which a metal ion, cobalt(II), a templating agent, pyridine, a ligand containing multidentate functional groups, BTC, and a ligand containing a monodentate functional group, pyridine, were combined to give a crystalline metal-organic microporous material. The reaction of BTC, $L_1$, with $Co^{2+}$, M, gave a material composed of Co-BTC 2D-sheets, with pyridine, $L_2$, bound axially to the metal ion. Specific interactions between the pyridine ligands produce a strong interaction, resulting in a rigid 3D structure.

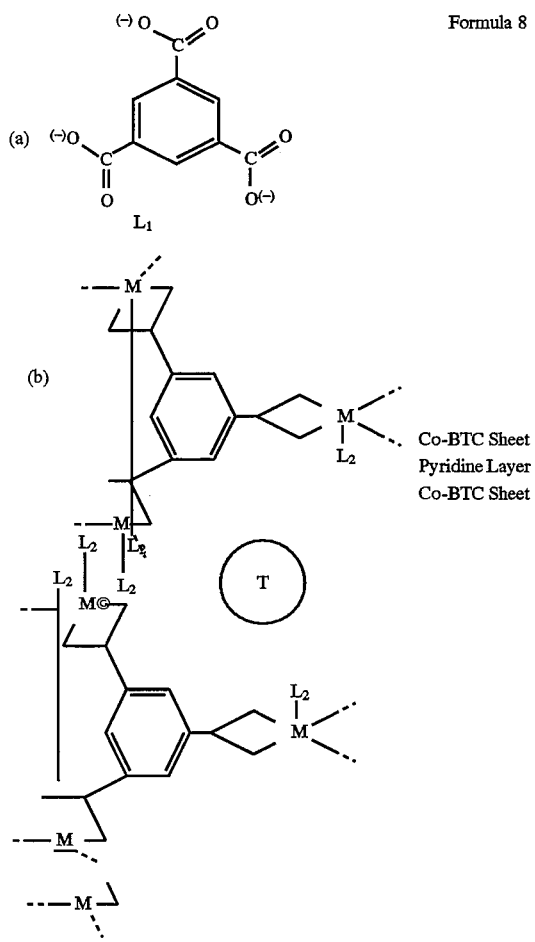

Formula 8

The stacking of the Co-BTC sheets in the crystal produce alternating Co-BTC and pyridine layers leading to voids where templating agents, T, and other adsorbed species are accommodated. Therefore, in this example pyridine is used as a pillar or spacer between the Co-BTC sheets. In this specific embodiment of the invention, pyridine was used both as the monodentate ligand and the templating agent. The consideration of other possible coordination modes of BTC points to a large number of possible structural variations. In addition, one can take advantage of metal ion coordination geometries other than octahedral, such as tetrahedral, square planar, linear, trigonal and trigonal bipyramidal.

It is understood that the ligands possessing multidentate functional groups bring with them corresponding counter cations, such as $H^+$, $Na^+$, $K^+$, $Mg^{2+}$, $Ca^{2+}$, $Sr^{2+}$, ammonium ion, alkylsubstituted ammonium ions, and arylsubstituted ammonium ions, or counter anions, such as $F^-$, $Cl^-$, $Br^-$, $I^{31}$, $ClO^-$, $ClO_2^-$, $ClO_3^-$, $ClO_4^-$, $OH^-$, $NO_3^-$, $NO_2^-$, $SO_4^{2-}$, $SO_3^{2-}$, $PO_4^{3-}$, and $CO_3^{2-}$.

The Metal Ions

The crystalline microporous materials of this invention can be synthesized using metal ions having distinctly different coordination geometries, in combination with a ligand possessing multidentate functional groups, and a suitable templating agent. Metal-organic microporous solids have been prepared using a metal ion that prefers octahedral coordination, cobalt(II), and a metal ion that prefers tetrahedral coordination, zinc(II), in the presence of the BTC ligand and a ligand containing a monodentate functional group. Therefore, it is reasonable to assume that stable metal-organic microporous materials can be made using metal ions from the following list: $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, and $Bi^{5+}$, $Bi^{3+}$, $Bi^+$; along with the corresponding metal salt counteranion. As used herein, the term metal ion refers to both metal and metalloid ions. Generally, the metal ions useful in this invention include: $Sc^{3+}$, $Ti^{4+}$, $V^{4+}$, $V^{3+}$, $V^{2+}$, $Cr^{3+}$, $Mo^{3+}$, $Mn^{3+}$, $Mn^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Al^{3+}$, $Ga^{3+}$, $In^{3+}$, $Ge^{4+}$, $Ge^{2+}$, $Sn^{4+}$, $Sn^{2+}$, $Pb^{4+}$, $Pb^{2+}$, $Sb^{5+}$, $Sb^{3+}$, $Sb^+$, and $Bi^{5+}$, $Bi^{3+}$, $Bi^+$; along with the corresponding metal salt counteranion. A preferred group of metal ions for use in this invention includes: $Sc^{3+}$, $Ti^{4+}$, $V^{4+}$, $V^{3+}$, $Cr^{3+}$, $Mo^{3+}$, $Mn^{3+}$, $Mn^{2+}$, $Fe^{3+}$, $Fe^{2+}$, $Co^{3+}$, $Co^{2+}$, $Ni^{2+}$, $Ni^+$, $Cu^{2+}$, $Cu^+$, $Ag^+$, $Zn^{2+}$, $Cd^{2+}$, $Al^{3+}$, $Sn^{4+}$, $Sn^{2+}$, and $Bi^{5+}$, $Bi^{3+}$, $Bi^+$; along with the corresponding metal salt counteranion. More preferably the metal ions useful in this invention are selected from the group consisting of: $Mn^{3+}$, $Mn^{2+}$, $Fe^{3+}$, $Fe^{2+}$, $Co^{3+}$, $Co^{2+}$, $Ni^{2+}$, $Ni^+$, $Cu^{2+}$, $Cu^+$, $Ag^+$, $Zn^{2+}$, $Cd^{2+}$, along with the corresponding metal salt counteranion. Most preferably the metal ions useful in this invention are selected from the group consisting of: $Fe^{3+}$, $Fe^{2+}$, $Co^{3+}$, $Co^{2+}$, $Ni^{2+}$, $Ni^+$, $Cu^{2+}$, $Cu^+$, $Zn^{2+}$, along with the corresponding metal salt counteranion. An especially preferred group of metals for use in this invention is: $Co^{3+}$, $Co^{2+}$, $Ni^{2+}$, $Ni^+$, $Zn^{2+}$, along with the corresponding metal salt counteranion.

The Templating Agent

The templating agents employed in this invention are added to the reaction mixture for the purpose of occupying the pores in the resulting crystalline metal-organic microporous materials. Examples of possible templating species are:

a. alkyl amines and their corresponding alkyl ammonium salts, containing linear, branched, or cyclic aliphatic groups, having from 1 to 20 carbon atoms;

b. aryl amines and their corresponding aryl ammonium salts having from 1 to 5 phenyl rings;

c. alkyl phosphonium salts, containing linear, branched, or cyclic aliphatic groups, having from 1 to 20 carbon atoms;

d. aryl phosphonium salts, having from 1 to 5 phenyl rings, e. alkyl organic acids and their corresponding salts, containing linear, branched, or cyclic aliphatic groups, having from 1 to 20 carbon atoms;

f. aryl organic acids and their corresponding salts, having from 1 to 5 phenyl rings;

g. aliphatic alcohols, containings linear, branched, or cyclic aliphatic groups, having from 1 to 20 carbon atoms;

h. aryl alcohols having from 1 to 5 phenyl rings;

i. inorganic anions from the group consisting of sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of said inorganic anions;

j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolmine, triethylamine, and trifluoromethylsulfonic acid.

The Process

The synthesis of the rigid and stable microporous materials of this invention can be carried out under extremely mild reaction conditions. In most cases, the reagents are combined into a solution, either aqueous or nonaqueous, with synthetic reaction temperatures ranging from 0° C. to 100° C. (in an open beaker). In other cases, solution reactions are carried out in a closed vessel at temperatures from 25° C. to 300° C. In either case, large single crystals or microcrystalline microporous solids are formed.

In the preparation of the materials of this invention, the reactants are generally added in a mole ratio of 1:10 to 10:1 metal ion to ligand containing multidentate functional groups. Preferably, the metal ion to ligand containing multidentate functional groups is 1:3 to 3:1, and most preferably from 1:2 to 2:1. The amount of templating agent is not critical, and in fact, templating agent can in some circumstances be employed as the solvent in which the reaction takes place. Templating agent can accordingly be employed in great excess without interfering with the reactions of this invention and the preparation of the microporous materials. When using a ligand containing monodentate functional groups in combination with the metal ion and the ligand containing multidentate functional groups, the ligand containing monodentate functional groups can be utilized in great excess. In certain circumstances the ligand containing monodentate functional groups can be utilized as the solvent in which the reaction takes place. In addition, in certain circumstances the ternplating agent and the ligand containing monodentate functional groups may be identical. An example of a templating agent which is a ligand containing monodentate functional groups is pyridine.

The preparation of the microporous materials of this invention is carried out in either an aqueous or non-aqueous system. The solvent may be polar or nonpolar as the case may be, and as stated earlier, the solvent may be the required ternplating agent, or the optional ligand containing a monodentate functional group. Examples of non-aqueous solvents include n-alkanes, such as pentane, hexane, benzene, toluene, xylene, chlorobenzene, nitrobenzene, cyanobenzene, aniline, naphthalene, naphthas, n-alcohols such as methanol, ethanol, n-propanol, isopropanol, acetone, 1,2,-dichloroethane, methylene chloride, chloroform, carbon tetrachloride, tetrahydrofuran, dimethylformamide, dimethylsulfoxide, thiophene, pyridine, ethanolamine, triethylamine, ethylenediamine, and the like. Those skilled in the art will be readily able to determine an appropriate solvent based on the starting reactants, and the choice of solvent is not believed to be critical in obtaining the microporous materials of this invention.

To aid in the formation of large single crystals of microporous materials, suitable for single crystal x-ray structural characterization, the solution reaction is performed in the presence of viscous materials, generally polymeric additives. Specific additives include polyethylene oxide, polymethylmethacrylic acid, silica gels, agar, fats, and collogens, which aid in achieving high yields and pure crystalline products. The growth of large single crystals of microporous materials leads to unambiguous characterization of the microporous framework. Large single crystals of microporous materials may be useful for magnetic and electronic sensing applications.

Examples

The following examples of this invention are meant as an illustration of the microporous materials that are obtained using the synthetic strategy defined by this invention, and are not meant to limit in any way the scope of the invention:

EXAMPLE 1

This example describes the synthesis of a stable microporous material from an ethanol/1,2-dichloroethane solution matrix at room temperature by the simple combination of a cobalt(II) salt with two select ligands, BTC, which possesses multidentate functional groups, and pyridine, which possesses a monodentate functional group, in the presence of a templating agent, pyridine. Solids of $Co(NO_3)_2 \cdot 6H_2O$ (0.582 g, 2 mmol) and BTC (0.420 g, 2 mmol) were dissolved in 15 mL ethanol, then added to a 5 mL solution of polyethylene oxide (PEO) (0.250 g, MW =100,000) in 1,2-dichloroethane. The mixture was stirred until a clear solution was obtained. This 20 mL reaction vessel was placed inside a larger vessel containing 1 mL of pyridine and the second vessel was closed. Gaseous pyridine was diffused into the reaction solution for three days, resulting in large, pink, cubed-shaped crystals in the 20 mL reaction vessel. These were collected and washed successively with 1,2-dichloroethane, ethanol, and acetone, resulting in a yield of 0.85 g (89 % yield). The density of crystals of this material that were freshly isolated from their mother liquor was measured by the floatation method to give a value of $1.484 \pm 0.01$ g cm$^{-3}$. Elemental analysis done on crystalline samples of this material: found; C, 54.99; H, 3.82; N, 7.44; Co, 12.43%: Calculated for $CoC_6H_3(COOH_{1/3})_3$ $(NC_5H_5)_2 \cdot 2/3$ $NC_5H_5$; C, 56.11; H, 3.66; N, 7.82; Co, 12.33%. These crystals are insoluble in water and common organic solvents.

The crystalline homogeneity of the microcrystalline product was confirmed by comparison of the observed (Table 1) and calculated (Table 2) x-ray powder diffraction patterns. The calculated x-ray powder diffraction pattern was produced using the single crystal data given below.

An x-ray crystal analysis study was performed on a single crystal obtained from this reaction. The x-ray diffraction pattern data is given in Table 3 which revealed the presence of a porous solid represented by the formula, $CoC_6H_3$ $(COOH\ 1/3)_3(NC_5H_5)_2 \cdot 2/3\ NC_5H_5$. Single crystals of this material are at 20±1° C., hexagonal, space group $P6_3/mcm$ – $D_{6h}^3$ (no. 193) with a=16.711(4)Å, c=14.189(2)Å, V=3423 (1)Å$^3$, and Z=6 {for x=1, $d_{calcd}$=1.464 g cm$^{-3}$, $\mu_a$(MoK$\overline{\alpha}$)=0.80 mm$^{-1}$}. A total of 1161 independent reflections having 2θ(MoK$\overline{\alpha}$)<50.7° (the equivalent of 0.8 limiting CuK$\alpha$spheres) were collected on a computer-controlled Nicolet autodifffactometer using full (0.90°-wide) co scans and graphite-monochromatic MoK$\overline{\alpha}$radiation. The structure was solved using "Direct Methods" techniques with the Siemens SHELXTL-PC software package as modified at Crystalytics Company. The resulting parameters have been refined to converge [$R_1$ (unweighted, based on F)=0.068 for 552 independent reflections having 2θ(MoK$\overline{\alpha}$)<50.7° and I>3σ(I)].

TABLE 1

| Peak | 2-Theta | d-Space | Intensity |
|---|---|---|---|
| 1 | 12.360 | 7.1554 | 62.03 |
| 2 | 16.260 | 5.4469 | 10.33 |
| 3 | 18.420 | 4.8128 | 100.00 |
| 4 | 21.320 | 4.1642 | 16.75 |
| 5 | 22.180 | 4.0047 | 11.22 |
| 6 | 25.000 | 3.5590 | 73.79 |
| 7 | 27.340 | 3.2594 | 8.47 |
| 8 | 28.300 | 3.1510 | 11.52 |
| 9 | 29.000 | 3.0765 | 15.24 |
| 10 | 32.220 | 2.7760 | 10.69 |
| 11 | 33.660 | 2.6605 | 8.31 |
| 12 | 38.940 | 2.3110 | 7.40 |
| 13 | 41.100 | 2.1944 | 7.43 |
| 14 | 43.400 | 2.0833 | 8.66 |

TABLE 2

| h | k | l | 2-theta | d-spacing | F | multi-plicity | Lp-factor | in-tensity |
|---|---|---|---|---|---|---|---|---|
| −1 | 2 | 1 | 12.29 | 7.2028 | 219.09 | 12 | 173.5965 | 100.00 |
| 0 | 0 | 2 | 12.46 | 7.1055 | 253.49 | 2 | 168.9132 | 21.71 |
| −1 | 3 | 0 | 16.20 | 5.4700 | 49.53 | 12 | 99.6912 | 2.94 |
| −1 | 3 | 1 | 17.37 | 5.1049 | 39.78 | 24 | 86.6968 | 3.29 |
| 0 | 2 | 2 | 17.49 | 5.0699 | 82.02 | 12 | 85.4990 | 6.90 |
| 0 | 3 | 0 | 18.39 | 4.8240 | 374.83 | 6 | 77.3128 | 65.18 |
| −1 | 3 | 2 | 20.49 | 4.3344 | 47.02 | 24 | 62.2186 | 3.30 |
| −2 | 4 | 0 | 21.27 | 4.1778 | 100.05 | 6 | 57.7308 | 3.47 |
| −1 | 2 | 3 | 21.56 | 4.1208 | 167.14 | 12 | 56.1408 | 18.82 |
| −1 | 4 | 0 | 22.15 | 4.0139 | 67.59 | 12 | 53.2116 | 2.92 |
| 0 | 3 | 2 | 22.27 | 3.9911 | 98.57 | 12 | 52.5996 | 6.13 |
| −2 | 4 | 2 | 24.72 | 3.6014 | 78.25 | 12 | 42.6381 | 3.13 |
| 0 | 0 | 4 | 25.06 | 3.5528 | 738.76 | 2 | 41.4670 | 45.26 |
| −1 | 4 | 2 | 25.49 | 3.4948 | 43.16 | 24 | 40.0919 | 1.79 |
| −2 | 5 | 0 | 26.85 | 3.3201 | 48.72 | 12 | 36.0848 | 1.03 |
| −1 | 2 | 4 | 37.28 | 3.2695 | 143.98 | 12 | 34.9607 | 8.70 |
| −1 | 5 | 0 | 28.26 | 3.1581 | 105.85 | 12 | 32.5500 | 4.38 |
| −1 | 5 | 1 | 28.96 | 3.0829 | 107.47 | 24 | 30.9696 | 8.58 |
| −1 | 3 | 4 | 29.99 | 2.9795 | 39.13 | 24 | 28.8585 | 1.06 |
| −1 | 5 | 2 | 30.99 | 2.8859 | 40.46 | 24 | 27.0101 | 1.06 |
| 0 | 3 | 4 | 31.27 | 2.8607 | 80.76 | 12 | 26.5223 | 2.08 |
| −3 | 6 | 0 | 32.14 | 2.7852 | 179.34 | 6 | 25.0865 | 4.84 |
| −3 | 6 | 1 | 32.77 | 2.7332 | 74.43 | 12 | 24.1200 | 1.60 |
| −1 | 2 | 5 | 33.30 | 2.6908 | 147.62 | 12 | 23.3457 | 6.11 |
| 0 | 5 | 2 | 33.43 | 2.6806 | 70.25 | 12 | 23.1607 | 1.37 |
| −1 | 5 | 3 | 34.12 | 2.6277 | 74.85 | 24 | 22.2147 | 2.99 |
| −3 | 6 | 2 | 34.59 | 2.5931 | 83.74 | 12 | 21.6064 | 1.82 |
| −1 | 6 | 2 | 36.82 | 2.4411 | 54.56 | 24 | 19.0280 | 1.36 |
| 0 | 0 | 6 | 37.99 | 2.3685 | 467.56 | 2 | 17.8516 | 7.81 |
| −2 | 7 | 0 | 38.86 | 2.3174 | 140.73 | 12 | 17.0444 | 4.05 |
| −2 | 7 | 1 | 39.39 | 2.2872 | 89.58 | 24 | 16.5754 | 3.19 |
| −1 | 2 | 6 | 39.55 | 2.2787 | 129.15 | 12 | 16.4450 | 3.29 |
| −2 | 7 | 2 | 40.96 | 2.2032 | 114.47 | 24 | 15.3034 | 4.81 |
| 0 | 3 | 6 | 42.52 | 2.1261 | 128.33 | 12 | 14.1772 | 2.80 |
| −1 | 5 | 5 | 42.80 | 2.1126 | 77.40 | 24 | 13.9848 | 2.01 |
| −4 | 8 | 0 | 43.31 | 2.0889 | 175.7 | 6 | 13.6483 | 2.53 |

Cu—K(alpha) radiation, 5.00 < 2-theta < 50.00
Intensity = F*F*LP*mult (scaled so that largest is 100)
Only results having intensities greater or equal to 1.00 are listed

TABLE 3

Atomic Coordinates for Nonhydrogen Atoms in Crystalline
$CoC_6H_3(COOH_{1/3})_3(NC_5H_5)_2 \cdot 2/3 NC_5H_5$
Obtained from Single Crystal x-ray analysis

| Atom Type[b] | Fractional Coordinates | | | Equivalent Isotropic Thermal Parameter, |
|---|---|---|---|---|
| | $10^4 x$ | $10^4 y$ | $10^4 z$ | $B.Å^2 \times 10^b$ |
| Co | 3246(2) | 0[c] | 2500[c] | 29(1) |
| $O_1$ | 2477(7) | 738(7) | 2500[c] | 54(4) |
| $C_1$ | 829(11) | 0[c] | 2500[c] | 22(6) |
| $C_2$ | 0[c] | −857(10) | 2500[c] | 26(6) |
| $C_3$ | 1779(15) | 0[c] | 2500[c] | 34(6) |
| $O_2$ | 4487(7) | 1136(7) | 2500[c] | 57(4) |
| $O_3$ | 5643(6) | 828(7) | 2500[c] | 57(5) |
| $C_4$ | 6023(10) | 2394(10) | 2500[c] | 27(5) |
| $C_5$ | 5736(9) | 3034(10) | 2500[c] | 24(5) |
| $C_6$ | 5307(8) | 1370(10) | 2500[c] | 29(5) |
| $N_{1s}$ | 3240(10) | 0[c] | 981(9) | 80(10) |
| $C_{1s}{}^d$ | 3557(32) | −236(37) | 456(26) | 101(38) |
| $C_{2s}$ | 3639(64) | −136(126) | −654(44) | 156(29) |
| $C_{3s}{}^d$ | 3388(38) | 397(32) | 885(30) | 94(21) |
| $C_{4s}{}^d$ | 3058(30) | 809(40) | −444(37) | 149(31) |
| $C_{5s}$ | 3051(31) | 752(30) | 646(20) | 101(22) |
| Templating Agents[e] | | | | |
| Molecule 1 | | | | |
| $C_{6s}$ | 455(7) | 910(14) | 0[c] | 125(32) |
| Molecule 2 | | | | |
| $C_{7s}$ | 6211(7) | 3789(7) | 0[c] | 171(388) |
| $C_{8s}$ | 7122(7) | 2878(7) | 0[c] | 217(388) |

[a]The numbers in parentheses are the estimated standard deviations in the last significant digit.
[b]For all atoms except $C_{2s}$, $C_{6s}$, $C_{7s}$ and $C_{8s}$ which were included in the structural model with isotropic thermal parameters, this is one-third of the trace of the orthogonalized $B_{ij}$ tensor. For atoms $C_{2s}$, $C_{6s}$, $C_{7s}$ and Cgs, this is the actual value of the refined isotropic thermal parameter.
[c]This is a symmetry-required value and is therefore listed without an estimated standard deviation.
[d]The pyridine molecules coordinate to the cobalt atoms were treated as being statistically-disordered-disordered with two preferred orientations about the Co—$N_{1s}$ bond the 16.711Å × 16.711Å × 14189Å hexagonal unit cell. One orientation is designated by atoms $N_{1s}$, $C_{1s}$, $C_{2s}$, $C_{3s}$, $C_{4s}$ and $C_{5S}$ (represented with solid bonds in FIG. 1) and the second orientation by atoms $N_{1s}$, $C_{1sc}$, $C_{2sc}$, $C_{3sc}$, $C_{4SC}$ and $C_{5sc}$ (represented with open bonds in FIG. 1). Carbon atoms were placed at these carbon sites with occupancy, factors that were half of their nominal values. A nitrogen atom until a full normal occupancy factor was included for $N_{1s}$.
[e]There appear to be two regions in the unit cell which contain disordered pyridine solvent molecules. Solvent molecules which consist of 6-membered carbon rings were therefore included in the structural model at these sites. The first of these (Solvent Molecule 1) is centered about the 3 m site at the origin of the mat cell and is generated from carbon atom $C_{6s}$. The second of these (Solvent Molecule 2) is centered about the 32 site at (2/3,113,0) in the unit cell and is generated from atoms $C_{7S}$ and $C_8$ Occupancy factors for carbon atoms placed at these positions were allowed to vary in refinement cycles and refined to final values of 0.22(2), 0.51(6) and 0.35(5) for carbon atoms $C_{6s}$, $C_{7s}$ and $C_{8s}$, respectively.

Using data from the x-ray single crystal analysis, a fragment of the structure of $CoC_6H_3(COOH_{1/3})_3(NC_5H_5)_2 \cdot 2/3\ NC_5H_5$ was generated and shown in Formula 9 where three BTC units are coordinated to each of the Co(II) centers. Formula 9 shows a single layer of the extended porous network of $CoC_6H_3(COOH_{1/3})_3(NC_5H_5)_2 \cdot 2/3\ NC_5H_5$. The hydrogen atoms on the pyridines and BTC units are omitted for clarity.

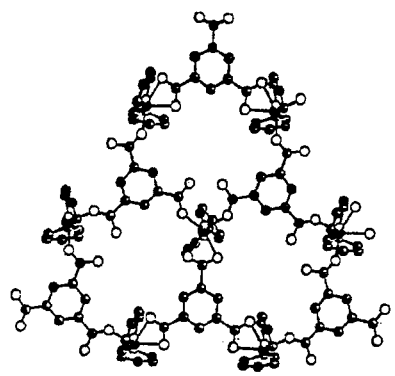

Formula 9

The axial positions of the cobalt ions are occupied by pyridine molecules. In the crystal, the Co-BTC sheets stack along the z-axis to give alternating cobalt-carboxylate layers and pyridine layers as shown in Formula 10. Formula 10 shows a perspective drawing of the solid state structure of $CoC_6H_3(COOH_{1/3})_3(NC_5H_5)_2 \cdot 2/3\ NC_5H_5$. The cobalt-carboxylate layers are shown anchored by pyridine ligands that are bound axially to cobalt. The pyridine ternplating agents (large spheres) reside in channels running between the layers.

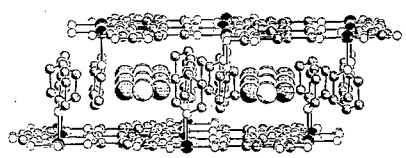

Formula 10

The cobalt-carboxylate layers are seperated by a distance of 7Å with the bound pyridine ligands holding these layers tightly together. The remaining space between the sheets contains the pyridine ternplating agents which occupy the rectangular channels (7×10Å). Since the layer-layer separation distance and the channel structure remain unaltered upon removal or inclusion of guests (vide infra), this compound is analogous to zeolites and not intercalation compounds.

EXAMPLE 2

The material prepared in EXAMPLE 1, $CoC_6H_3(COOH_{1/3})_3(NC_5H_5)_2 \cdot 2/3\ NC_5H_5$, was also prepared in the absence of the viscous medium, PEO. Solids of $Co(NO_3)_2 \cdot 6H_2O$ (0.30 g, 1 mmol) and BTC (0.21 g, 1 mmol) were dissolved in a 20 mL reaction vessel using 10 mL of ethanol. This 20 mL reaction vessel was placed inside a larger vessel containing 1 mL of pyridine and the second vessel was closed. Gaseous pyridine was allowed to diffuse into the reaction solution for three days, resulting in pink, cubed-shaped crystals in the 20 mL reaction vessel. These were collected and washed successively with ethanol and acetone, and air dried, resulting in a yield of 0.26 g (56 % yield). The x-ray powder diffraction data collected for the product of this reaction, were identical to that from the product obtained in EXAMPLE 1, $CoC_6H_3(COOH_{1/3})_3(NC_5H_5)_2 \cdot 2/3\ NC_5H_5$, confirming that the same crystalline microporous material was prepared regardless of the presence of the viscous PEO medium.

EXAMPLE 3

The stacking of the pyridine ligands axially coordinated to the cobalt metal centers in the microporous material described in EXAMPLE 1, $CoC_6H_3(COOH_{1/3})_3(NC_5H_5)_2 \cdot 2/3\ NC_5H_5$, has significant implications on the three-dimensional rigidity and stability of the material. Thermal gravimetric analysis, shown in FIG. 1, performed on a crystalline sample of $CoC_6H_3(COOH_{1/3})_3(NC_5H_5)_2 \cdot 2/3\ NC_5H_5$ showed cleanly a weight loss of 11.7% at 190° C., corresponding to the loss of the pyridine templating agents (2/3 $NC_5H_5$ per formula unit). Decomposition of the material did not occur until 350° C., as evidenced by another weight loss of a total 45.5% corresponding to the remaining pyridine molecules bound to the cobalt metal centers (2 remaining $NC_5H_5$ per formula unit).

This material does not lose its crystallinity or become altered to a different framework structure upon removal of the pyridine templating agents. The material was shown to remain intact up to 200° C. for as long as four hours, as confirmed by x-ray powder diffraction data. Table 4 shows that the positions of the most intense lines are unchanged from those of the unheated sample (compare with Table 1). Elemental analysis of the material heated to 200° C. confirms the absence of pyridine templating agents and the retention of the axially bound pyridines (found; C, 52.38; H, 3.46; N, 6.84%: Calculated for $CoC_6H_3(COOH_{1/3})_3(NC_5H_5)_2$; C, 53.66; H, 3.32; N, 6.59).

TABLE 4

| Peak | 2-Theta | d-Space | Intensity |
|---|---|---|---|
| 1 | 10.56 | 8.3707 | 11.14 |
| 2 | 12.34 | 7.1670 | 55.65 |
| 3 | 16.54 | 5.3553 | 12.84 |
| 4 | 18.40 | 4.8179 | 100.00 |
| 5 | 21.32 | 4.1642 | 16.17 |
| 6 | 22.32 | 3.9799 | 10.58 |
| 7 | 24.90 | 3.5730 | 63.27 |
| 8 | 27.28 | 3.2665 | 12.34 |
| 9 | 28.24 | 3.1576 | 13.61 |
| 10 | 29.02 | 3.0744 | 13.21 |
| 11 | 32.16 | 2.7811 | 14.25 |
| 12 | 33.74 | 2.6544 | 10.27 |
| 13 | 34.76 | 2.5788 | 11.54 |
| 14 | 38.98 | 2.3088 | 10.75 |
| 15 | 43.40 | 2.0833 | 9.71 |

EXAMPLE 4

Figure 2:
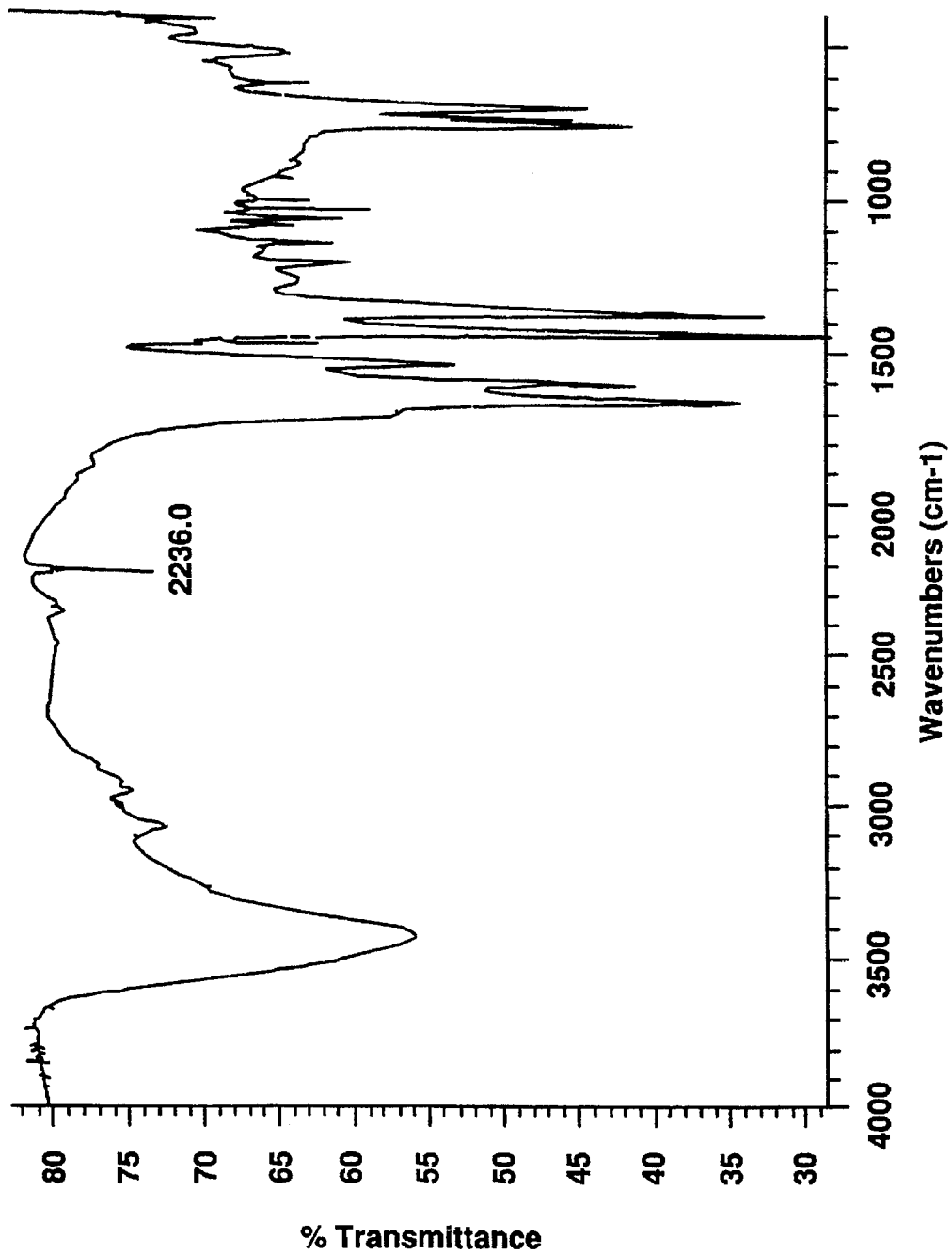
FIG. 2 is a FTIR spectrum of CoC$_6$H$_3$(COOH$_{1/3}$)$_3$(NC$_5$H$_5$)$_2$ with cyanobenzene absorbed into the framework.

Based on infrared data and elemental analysis, solid samples of the template-free material discussed in EXAMPLE 2, $CoC_6H_3(COOH_{1/3})_3(NC_5H_5)_2$, selectively adsorb aromatic molecules such as benzene, nitrobenzene, cyanobenzene, and chlorobenzene, in the presence of acetonitrile, nitromethane, or dichloroethane. Such experiments were performed by suspending $CoC_6H_3(COOH_{1/3})_3(NC_5H_5)_2$ in a solvent mixture containing an aromatic and an aliphatic component, such as $C_6H_5CN/CH_3CN$, for approximately 30 minutes, followed by filtration and air drying. FIG. 2 shows results for the case of $C_6H_5CN/CH_3CN$, in which the FT IR spectrum of the resulting solid showed a peak at 2236 cm$^{-1}$ corresponding to the $v_{CN}$ of $C_6H_5CN$, with no peak appearing at 2260 or 2300 cm$^{-1}$ where acetonitrile $v_{CN}$ peaks appear. The small peaks between 2300–2400 cm$^{-1}$ are due to atmospheric carbon dioxide.

Figure 3:
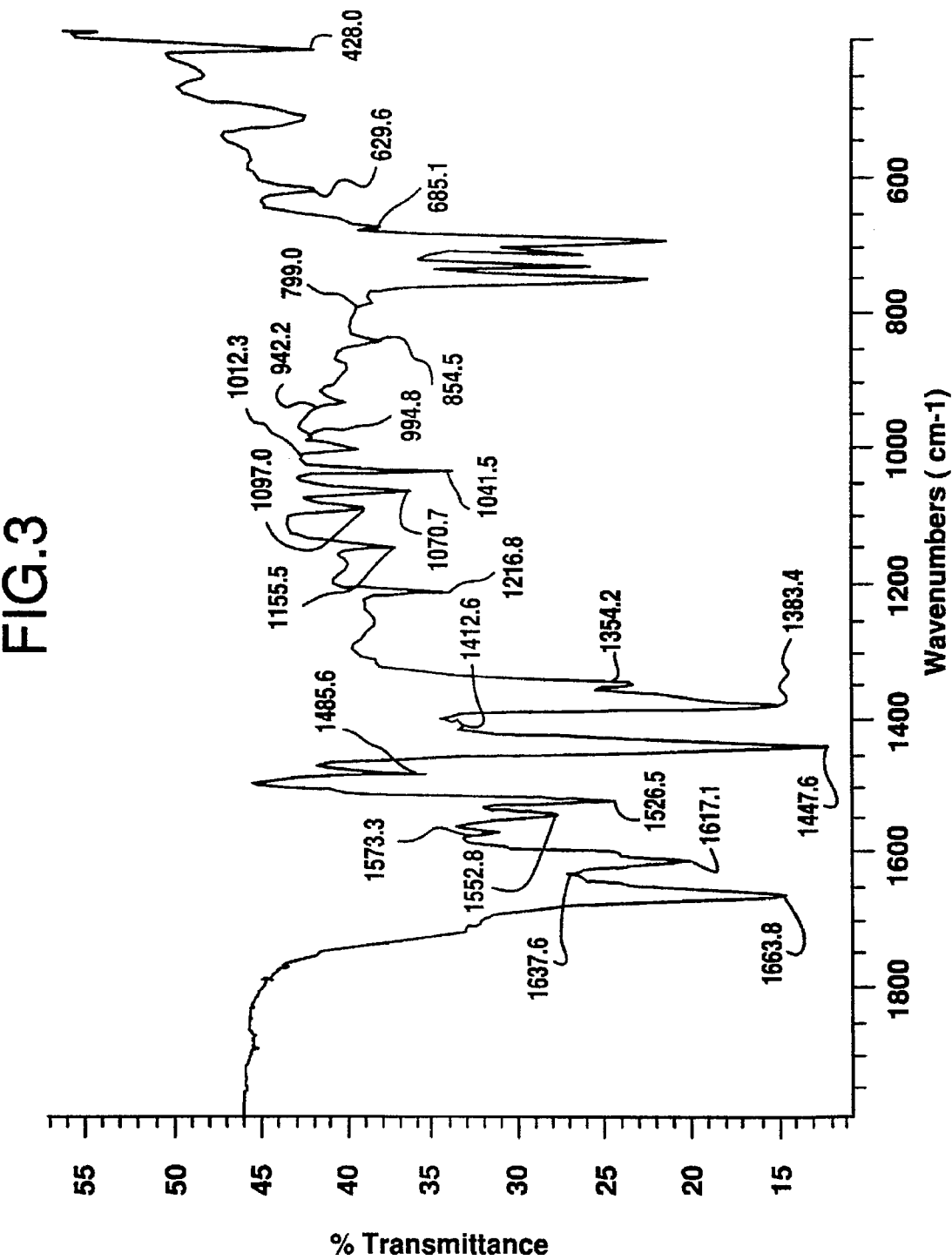
FIG. 3 is a FTIR spectrum of CoC$_6$H$_3$(COOH$_{1/3}$)$_3$(NC$_5$H$_5$)$_2$ with nitrobenzene absorbed into the framework.

FIG. 3 shows results from an analogous experiment done using the $C_6H_5NO_2/CH_3NO_2$ mixture. In this case, the FT IR spectrum of the resulting solid showed peaks at 1526, 1354, 854, and 685 cm$^{-1}$, corresponding to that of $C_6H_5NO_2$, with no peaks appearing at 1570, 1406, 1386, 1103, or 662 cm$^-$, where nitromethane peaks appear.

Figure 4:
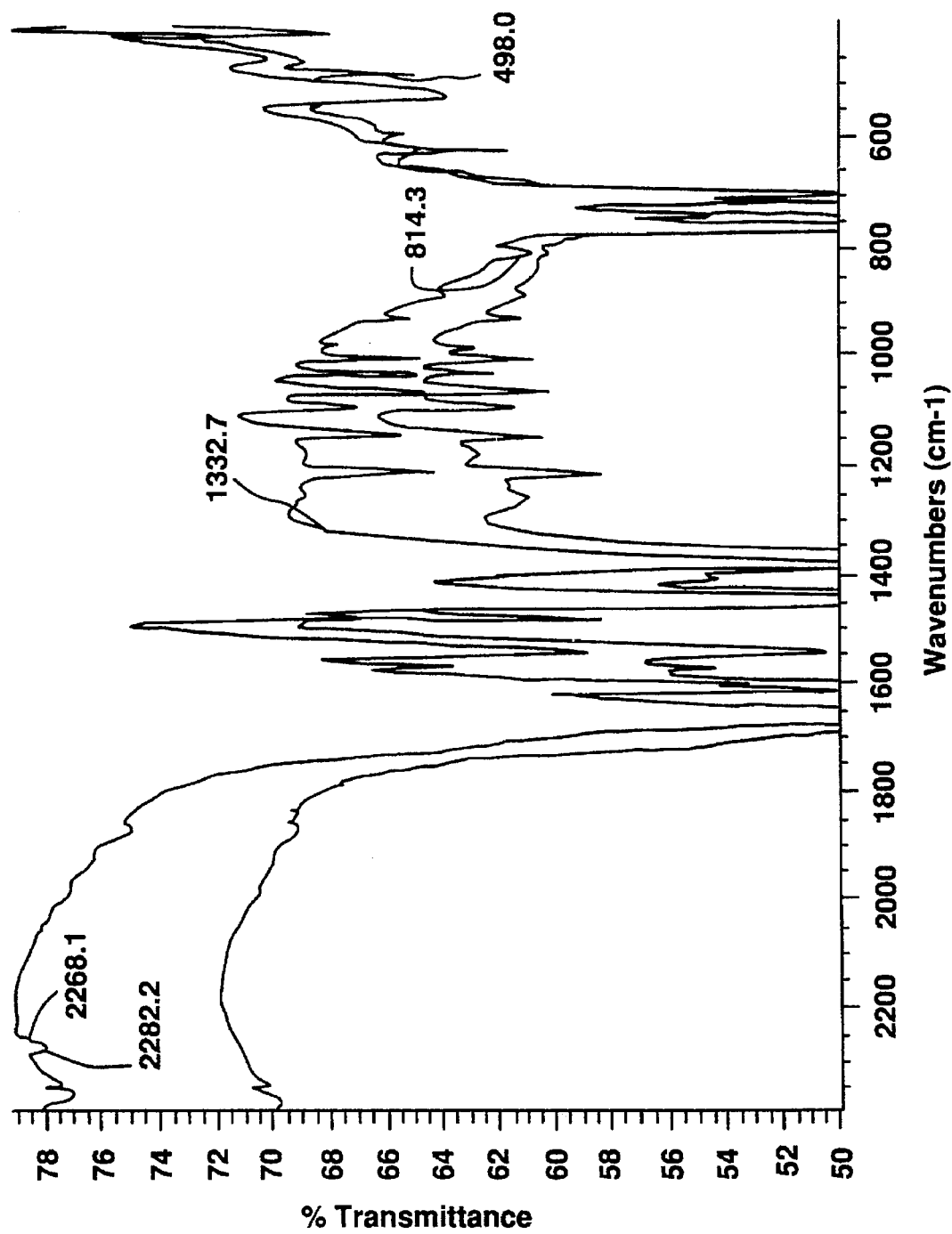
FIG. 4 is an overlay of FTIR spectra of COC$_6$H$_3$(COOH$_{1/3}$)$_3$ (NC$_5$H$_5$)$_2$ and CoC$_6$H$_3$(COOH$_{1/3}$)$_3$ (NC$_5$H$_5$)$_2$ with C$_6$D$_6$ absorbed into the framework.

FIG. 4 shows results from the inclusion of benzene into $CoC_6H_3(COOH_{1/3})_3(NC_5H_5)_2$. FIG. 4 shows an overlay of FTIR spectra, with the thinly traced FTIR spectrum being that of $CoC_6H_3(COOH_{1/3})_3(NC_5H_5)_2$, and the more boldly traced FTIR spectrum being that of the material after about 30 minutes of submersion in benzene solvent. The peaks at 2282, 2268, 1332, 814 and 498 cm$^{-1}$ are consistent with benzene adsorption into the microporous material.

Alternatively, the pyridine ternplating agents can be exchanged by suspending a crystalline sample of $CoC_6H_3(COOH_{1/3})_3(NC_5H_5)_2 \cdot 2/3\ NC_5H_5$ at 60° C. for one day in the aromatic solvent to be adsorbed, as evidenced from the FTIR spectrum. The solid remains intact and is rigid, as evidenced from the x-ray powder diffraction pattern, which is similar to that of the original starting material.

EXAMPLE 5

This example describes the synthesis of a stable microporous material in an ethanol/1,2-dichloroethane solution matrix by the simple combination of a zinc(II) salt with select ligands, BTC, which possesses multidentate functional groups, nitrate, which possesses a monodentate functional group, and triethylamine as solvent. Solids of $Zn(NO_3)_2 \cdot 6H_2O$ (0.60 g, 2 mmol) and BTC (0.21 g, 1 mmol) were dissolved in ethanol. This solution was added to a 2 mL 1,2-dichloroethane solution containing polyethylene oxide (0.12 g, MW=100,000). Upon stirring, the solution became clear and a gel was formed. This reaction vessel was placed inside a larger vessel containing 1 mL of triethylamine and the second vessel was closed. After 2–3 days, colorless cubic crystals appeared. The solid was collected and washed successively with ethanol and was air dried to give 0.30 g of product (70% yield). Elemental analysis done on crystalline samples of this material found: C, 24.40; H, 3.20; N, 2.91: calculated for $Zn_2(C_9H_3O_6) \cdot NO_3(H_2O)_{3.5}(C_2H_5OH)_{0.5}$; C, 24.71; H, 2.70; N, 2.88.

X-ray diffraction studies perfomed on single crystals obtained from this reaction revealed the existence of a crystalline microporous material composed of $Zn_2(C_9H_3O_6) \cdot NO_3(H_2O)_{3.5}(C_2H_5OH)_{0.5}$ Single crystals of this material are at 20±1° C., cubic, space group P2(1)3, with a=14.720 (2)Å. Table 5 shows the atomic coordinates for the material which were obtained from single crystal x-ray analysis. The structure of $Zn_2(C_9H_3O_6) \cdot NO_3(H_2O)_{3.5}(C_2H_5OH)o.5$ is constructed from the units shown in Formula 11a, which form large rings of zinc(II) and BTC, that are fused together (Formula 11b) to give the channel network (Formula 11c). The nitrate is bound to zinc and is pointing toward the center of the channels. The templating agent, ethanol, occupies the remaining space in the channels. The ethanol templating agents and the hydrogens on the carbon atoms of the BTC ligand are omitted for clarity.

TABLE 5

| Atom Type | Fractional Coordinates | | |
|---|---|---|---|
|  | $10^4 x$ | $10^4 y$ | $10^4 z$ |
| ZN1 | −0.18741 | −0.18741 | −0.18741 |
| ZN2 | −0.04685 | −0.04685 | −0.04685 |
| O1 | −0.20588 | −0.17977 | −0.05145 |
| O2 | −0.15931 | −0.05261 | 0.02219 |
| C1 | −0.21400 | −0.12517 | 0.00715 |
| C2 | −0.29040 | −0.12700 | 0.07924 |
| C3 | −0.34760 | −0.20374 | 0.07023 |
| H3 | −0.33996 | −0.24655 | 0.02163 |
| O1E | −0.32779 | −0.17555 | −0.20343 |
| C1E | −0.38780 | −0.06827 | −0.19122 |
| H1EA | −0.44421 | −0.08243 | −0.22073 |
| H1EB | −0.35775 | −0.02266 | −0.22687 |
| C2E | −0.42678 | −0.06280 | −0.08996 |
| O1S | −0.55566 | 0.20844 | −0.35979 |
| C2S | −0.46465 | 0.17157 | −0.29759 |
| C3S | −0.45398 | 0.21116 | −0.22956 |
| O2S | −0.56675 | 0.18980 | −0.22085 |

TABLE 5-continued

| Atom | Fractional Coordinates | | |
|---|---|---|---|
| Type | $10^4 x$ | $10^4 y$ | $10^4 z$ |
| O3S | −0.56571 | 0.16314 | −0.31344 |
| O3 | 0.0494 | 0.0494 | 0.0494 |

Formula 11

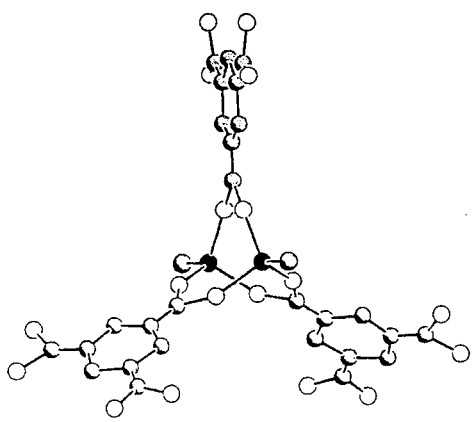

(a)

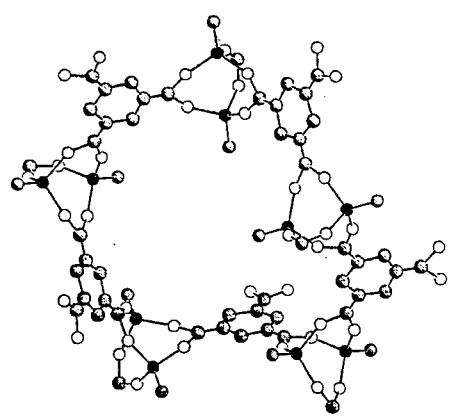

(b)

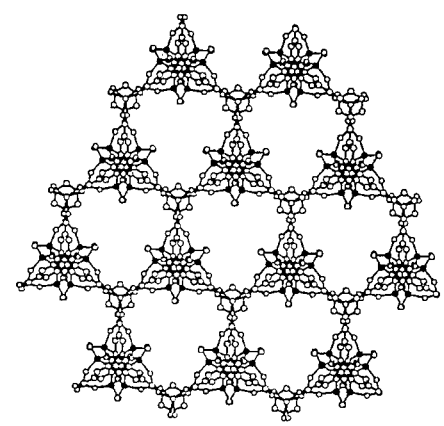

(c)

EXAMPLE 6

The material prepared in EXAMPLE 5, $Zn_2(C_9H_3O_6)$ $\cdot NO_3(H_2O)_{3.5}(C_2H_5OH)_{0.5}$ was also prepared in the absence of the viscous medium, PEO. Solids of $Zn(NO_3)_2 \cdot 6H_2O$ (0.30 g, 1 mmol) and BTC (0.105 g, 0.5 mmol) were dissolved in a 20 mL reaction vessel using 10 mL of ethanol. In another 5 mL vessel, 2 mL of triethylamine were added. The vessels were placed side-by-side in a larger container, which was then closed. Gaseous triethylamine was allowed to diffuse into the 10 mL reaction solution for one day, resulting in colorless crystals in the 20 mL reaction vessel. After three days these were collected and washed successively with ethanol and acetone, resulting in a yield of 0.18 g (80% yield). Due to the large pore sizes in this microporous material, solvent molecules in the pores were lost very quickly, with a 30% weight loss occurring in one day. The x-ray diffraction data collected for the product of this reaction were identical to that from the product obtained in EXAMPLE 5, $Zn_2(C_9H_3O_6) \cdot NO_3(H_2O)_{3.5}(C_2H_5OH)_{0.5}$.

Having thus described my invention, I claim:

1. A method for the preparation of microporous materials which comprises the steps of:

Admixing a solution containing one or more metal ions from the group consisting of:

$Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $C^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pt^{+}$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, and $Bi^{5+}$, $Bi^{3+}$, $Bi^{+}$; along with the corresponding metal salt counteranion, with one or more ligands having at least one of:

an alkyl group substructure, having from 1 to 10 carbon atoms; an aryl group substructure, having from 1 to 5 phenyl rings; or, an alkyl or aryl amine substructure, consisting of alkyl groups having from 1 to 10 carbon atoms or aryl groups having from 1 to 5 phenyl rings, said ligand substructure having bound thereto multidentate functional groups, X, which are covalently bound to the substructure of the ligand, wherein X is a functional group selected from the groups consisting of:

$CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$; $CH(SH)_2$, $C(SH)_3$, $CH(NH_2)_2$, $C(NH_2)_3$, $CH(OH)_2$, $C(OH)_3$, $CH(CN)_2$, $C(CN)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings, in the presence of a templating agent, selected from the group consisting of:

a. alkyl amines and their corresponding alkyl ammonium salts, containing linear, branched, or cyclic aliphatic groups, having from 1 to 20 carbon atoms;

b. aryl amines and their corresponding aryl ammonium salts having from 1 to 5 phenyl rings;

c. alkyl phosphonium salts, containing linear, branched, or cyclic aliphatic groups, having from 1 to 20 carbon atoms;

d. aryl phosphonium salts, having from 1 to 5 phenyl rings, e. alkyl organic acids and their corresponding salts, containing linear, branched, or cyclic aliphatic groups, having from 1 to 20 carbon atoms;

f. aryl organic acids and their corresponding salts, having from 1 to 5 phenyl rings;

g. aliphatic alcohols, containings linear, branched, or cyclic aliphatic groups, having from 1 to 20 carbon atoms;

h. aryl alcohols having from 1 to 5 phenyl rings;

i. inorganic anions from the group consisting of sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of said inorganic anions;

j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine,and trifluoromethylsulfonic acid.

2. The method of claim 1 wherein the templating agent is pyridine.

3. The method of claim 1 wherein the templating agent is ethanol.

4. The method of claim 1 wherein the ligand is benzene-1,3,5-tricarboxylic acid.

5. The method of claim 1 wherein the ligand is benzene-1,4-dicarboxylic acid.

6. The method of claim 1 wherein the ligand is benzene-1,2,4,5-tetracarboxylic acid.

7. The method of claim 1 wherein the ligand is adamantane-1,3,5,7-tetracarboxylic acid.

8. The method of claim 1 wherein the ligand is 1,1',1",1'''-methanetetracarboxylic acid.

9. The method of claim 1 wherein the microporous materials are prepared in the presence of a ligand containing one or more monodentate functional groups said ligand selected from the group consisting of:

a. alkyl amines containing at least one alkyl group containing 1 to 10 carbon atoms;

b. aryl amines containing from 1 to 5 phenyl rings;

c. alkyl alcohols containing at least one alkyl group having from 1 to 10 carbon atoms;

d. aryl alcohols containing from 1 to 5 phenyl rings;

e. alkyl thiols containing at least one alkyl group having from 1 to 10 carbon atoms;

f. aryl thiols containing from 1 to 5 phenyl rings;

g. alkyl cyanides containing at least one alkyl group having from 1 to 10 carbon atoms;

h. aryl cyanides containing from 1 to 5 phenyl rings; and i. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, thiocyanide, and isonitrile, and the corresponding acids and salts of said inorganic anions.

10. The method of claim 9 wherein the ligand containing one or more monodentate functional groups is selected from the group consisting of: pyridine, 4,4'-bipyridine, ethylenediamine, propylenediamine, 2-aminoethanol, 3-aminopropanol, trimethylamine, triethylamine, tripropylamine, 2-aminopropane, triethanolamine, ethylbutylamine, piperidine, cyclohexylamine, 2-methylpyridine, N,N-dimethylbenzylamine, N,N-dimethylethanolamine, N,N'-dimethylpiperazine, N-methyldiethanolamine, N-methylethanolamine, N-methylpiperidine, 3-methyl-piperidine, 4-methylpyridine, 1,4-diaminocyclohexane, morpholine, aniline, 1,4-diaminobenzene, 1,3,5-triaminobenzene, 1,3,5-triazine, imidazole, pyrazine, methanol, dihydroxymethane, trihydroxymethane, tetrahydroxymethane, ethanol, ethylene glycol, 1,1,2,2-tetrahydroxyethane, 1-propanol, 2-propanol, propylene glycol, 1,3-propanediol, glycerol, 1,1,3,3-tetrahydroxypropane, allyl alcohol, n-butanol, sec-butanol, iso-butanol, tert-butanol, 1,4-butanediol, 1,3-butanediol, 1,1,4,4-tetrahydroxybutane, n-pentanol, sec-pentanol, iso-pentanol, tert-pentanol, 1,5-pentanediol, 1,4-pentanediol, 1,3-pentanediol, 1,3,5-trihydroxypentane, n-hexanol, sec-hexanol, iso-hexanol, tert-hexanol, 1,6-hexanediol, 1,5-hexanediol, 1,4-hexanediol, 1,3-hexanediol, 1,3,6-trihydroxyhexane, cyclohexanol, 1,4-dihydroxycyclohexane, 1,3,5-trihydroxycyclohexane, phenol, benzyl alcohol, hydroquinone, catechol, resorcinol, 1,3,5-trihydroxybenzene, 1,2,4-trihydroxy-benzene, 1,2,3-trihydroxybenzene, 1,2,4,5-tetrahydroxybenzene, thiomethane, thioethane, thiopropane, thiocyclohexane, thiobenzene, 1,3-dithiopropane, 1,4-dithiobutane, 1,4-dithiobenzene, and 1,3,5-trithiobenzene, 1,4-dicyanobenzene, and 1,3,5-tricyanobenzene.

11. The method according to claim 1 in which the reaction mixture containing the microporous material product is heated from 30° C. to 500° C. to partially or completely remove the templating agent.

12. A method for the preparation of microporous materials which comprises the steps of:

Admixing a solution containing one or more metal ions from the group consisting of:

$Sc^{3+}$, $Ti^{4+}$, $V^{4+}$, $V^{3+}$, $V^{2+}$, $Cr^{3+}$, $Mo^{3+}$, $Mn^{3+}$, $Mn^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pt^{+}$, $Cu^{2+}$, $Cu^{+}$, $Ag^{+}$, $Au^{+}$, $Zn^{2+}$, $Cd^{2+}$, $Al^{3+}$, $Ga^{3+}$, $In^{3+}$, $Ge^{4+}$, $Ge^{2+}$, $Sn^{4+}$, $Sn^{2+}$, $Pb^{4+}$, $Pb^{2+}$, $Sb^{5+}$, $Sb^{3+}$, $Sb^{+}$, and $Bi^{5+}$, $Bi^{3+}$, $Bi^{+}$; along with the corresponding metal salt counteranion with, one or more ligand substructures being at least one of: methane, tetraphenylmethane, ethylene, tertiary amines, tertiary alkyl mines having from 1 to 3 carbon atoms, tertiary aryl amines having from 1 to 2 phenyl rings, benzene, naphthylene, adamantane, squarane, alkanes having from 2 to 4 carbon atoms, and alkenes having from 2 to 4 carbon atoms, said ligand substructure having bound thereto multidentate functional groups, X, which are covalently bound to the substructure of the ligand, wherein X is a functional group selected from the groups consisting of:

COOH, CSSH, $CH(RSH)_2$, $CH(RNH_2)_2$, $CH(ROH)_2$, and $CH(RCN)_2$, wherein R is H or an alkyl group having from 1 to 3 carbon atoms, or an aryl group consisting of one phenyl ring in the presence of a templating agent, selected from the group consisting of:

a. alkyl amines and their corresponding alkyl ammonium salts, containing linear, branched, or cyclic aliphatic groups, having from 1 to 20 carbon atoms;

b. aryl mines and their corresponding aryl ammonium salts having from 1 to 5 phenyl rings c. alkyl phosphonium salts, containing linear, branched, or cyclic aliphatic groups, having from 1 to 20 carbon atoms;

d. aryl phosphonium salts, having from 1 to 5 phenyl rings, e. alkyl organic acids and their corresponding salts, containing linear, branched, or cyclic aliphatic groups, having from 1 to 20 carbon atoms;

f. aryl organic acids and their corresponding salts, having from 1 to 5 phenyl rings;

g. aliphatic alcohols, containings linear, branched, or cyclic aliphatic groups, having from 1 to 20 carbon atoms;

h. aryl alcohols having from 1 to 5 phenyl rings;

i. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of said inorganic anions;

j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine,and trifluoromethylsulfonic acid.

13. The method of claim 12 wherein the templating agent is pyridine.

14. The method of claim 12 wherein the templating agent is ethanol.

15. The method of claim 12 wherein the ligand is benzene-1,3,5-tricarboxylic acid.

16. The method of claim 12 wherein the ligand is benzene-1,4-dicarboxylic acid.

17. The method of claim 12 wherein the ligand is benzene-1,2, 4, 5-tetracarboxylic acid.

18. The method of claim 12 wherein the ligand is adamantane-1,3,5,7-tetracarboxylic acid.

19. The method of claim 12 wherein the ligand is 1,1',1",1'"-methanetetracarboxylic acid.

20. The method of claim 12 wherein the microporous materials are prepared in the presence of a ligand containing one or more monodentate functional groups said ligand selected from the group consisting of:

a. alkyl amines containing at least one alkyl group containing 1 to 10 carbon atoms;

b. aryl amines containing from 1 to 5 phenyl rings;

c. alkyl alcohols containing at least one alkyl group having from 1 to 10 carbon atoms;

d. aryl alcohols containing from 1 to 5 phenyl rings;

e. alkyl thiols containing at least one alkyl group having from 1 to 10 carbon atoms;

f. aryl thiols containing from 1 to 5 phenyl rings;

g. alkyl cyanides containing at least one alkyl group having from 1 to 10 carbon atoms;

h. aryl cyanides containing from 1 to 5 phenyl rings; and i. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, thiocyanide, and isonitrile, and the corresponding acids and salts of said inorganic anions.

21. The method of claim 20 wherein the ligand containing one or more monodentate functional groups is selected from the group consisting of: pyridine, 4,4'-bipyridine, ethylenediamine, propylenediamine, 2-aminoethanol, 3-aminopropanol, trimethylamine, triethylamine, tripropylamine, 2-aminopropane, triethanolamine, ethylbutylamine, piperidine, cyclohexylamine, 2-methylpyridine, N,N-dimethylbenzylamine, N,N-dimethylethanolamine, N,N'-dimethylpiperazine, N-methyldiethanolamine, N-methylethanolamine, N-methylpiperidine, 3-methyl-piperidine, 4-methylpyridine, 1,4-diaminocyclohexane, morpholine, aniline, 1,4-diaminobenzene, 1,3,5-triaminobenzene, 1,3,5-triazine, imidazole, pyrazine, methanol, dihydroxymethane, trihydroxymethane, tetrahydroxymethane, ethanol, ethylene glycol, 1,1,2,2-tetrahydroxyethane, 1-propanol, 2-propanol, propylene glycol, 1,3-propanediol, glycerol, 1,1,3,3-tetrahydroxypropane, allyl alcohol, n-butanol, sec-butanol, iso-butanol, tert-butanol, 1,4-butanediol, 1,3-butanediol, 1,1,4,4-tetrahydroxybutane, n-pentanol, sec-pentanol, iso-pentanol, tert-pentanol, 1,5-pentanediol, 1,4-pentanediol, 1,3-pentanediol, 1,3,5-trihydroxypentane, n-hexanol, sec-hexanol, iso-hexanol, tert-hexanol, 1,6-hexanediol, 1,5-hexanediol, 1,4-hexanediol, 1,3-hexanediol, 1,3,6-trihydroxyhexane, cyclohexanol, 1,4-dihydroxycyclohexane, 1,3,5-trihydroxycyclohexane, phenol, benzyl alcohol, hydroquinone, catechol, resorcinol, 1,3,5-trihydroxybenzene, 1,2,4-trihydroxybenzene, 1,2,3-trihydroxybenzene, 1,2,4,5-tetrahydroxybenzene, thiomethane, thioethane, thiopropane, thiocyclohexane, thiobenzene, 1,3-dithiopropane, 1,4-dithiobutane, 1,4-dithiobenzene, and 1,3,5-trithiobenzene, 1,4-dicyanobenzene, and 1,3,5-tricyanobenzene.

22. The method according to claim 12 in which the reaction mixture containing the microporous material product is heated from 30° C. to 500° C. to partially or completely remove the templating agent.

23. A method for the preparation of microporous materials which comprises the steps of:

Admixing a solution containing one or more metal ions from the group consisting of:

$Sc^{3+}, Ti^{4+}, V^{4+}, V^{3+}, Cr^{3+}, Mo^{3+}, Mn^{3+}, Mn^{2+}, Fe^{3+}, Fe^{2+}, Co^{3+}, Co^{2+}, Ni^{2+}, Ni^{+}, Cu^{2+}, Cu^{+}, Ag^{+}, Zn^{2+}, Cd^{2+}, Al^{3+}, Sn^{4+}, Sn^{2+},$ and $Bi^{5+}, Bi^{3+}, Bi^{+}$; along with the corresponding metal salt counteranion with, one or more ligand substructures being at least one of: methane, tetraphenylmethane, ethylene, benzene, naphthylene, adamantane, and squarane; said ligand substructure having bound thereto multidentate functional groups, X, which are covalently bound to the substructure of the ligand, wherein X is a functional group selected from the groups consisting of:

COOH, CSSH, $CH(RSH)_2$, $CH(RNH_2)_2$, $CH(ROH)_2$, and $CH(RCN)_2$, wherein R is H or methyl or an aryl group consisting of one phenyl ring. in the presence of a ternplating agent, selected from the group consisting of:

a. alkyl amines and their corresponding alkyl ammonium salts, containing linear, branched, or cyclic aliphatic groups, having from 1 to 20 carbon atoms;

b. aryl amines and their corresponding aryl ammonium salts having from 1 to 5 phenyl rings c. alkyl phosphonium salts, containing linear, branched, or cyclic aliphatic groups, having from 1 to 20 carbon atoms;

d. aryl phosphonium salts, having from 1 to 5 phenyl rings, e. alkyl organic acids and their corresponding salts, containing linear, branched, or cyclic aliphatic groups, having from 1 to 20 carbon atoms;

f. aryl organic acids and their corresponding salts, having from 1 to 5 phenyl rings;

g. aliphatic alcohols, containings linear, branched, or cyclic aliphatic groups, having from 1 to 20 carbon atoms;

h. aryl alcohols having from 1 to 5 phenyl rings;

i. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of said inorganic anions; ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylene-chloride, tetrahydrofuran, ethanolamine, triethylamine, and trifluoro-methylsulfonic acid.

24. The method of claim 23 wherein the templating agent is pyridine.

25. The method of claim 23 wherein the templating agent is ethanol.

26. The method of claim 23 wherein the ligand is benzene-1,3,5-tricarboxylic acid.

27. The method of claim 23 wherein the ligand is benzene-1,4-dicarboxylic acid.

28. The method of claim 23 wherein the ligand is benzene-1,2, 4, 5-tetracarboxylic acid.

29. The method of claim 23 wherein the ligand is adamantane-1,3,5,7-tetracarboxylic acid.

30. The method of claim 23 wherein the ligand is 1,1',1'',1'''-methanetetracarboxylic acid.

31. The method of claim 23 wherein the microporous materials are prepared in the presence of a ligand containing one or more monodentate functional groups said ligand selected from the group consisting of:

a. alkyl amines containing at least one alkyl group containing 1 to 10 carbon atoms;

b. aryl amines containing from 1 to 5 phenyl rings;

c. alkyl alcohols containing at least one alkyl group having from 1 to 10 carbon atoms;

d. aryl alcohols containing from 1 to 5 phenyl rings;

e. alkyl thiols containing at least one alkyl group having from 1 to 10 carbon atoms;

f. aryl thiols containing from 1 to 5 phenyl rings;

g. alkyl cyanides containing at least one alkyl group having from 1 to 10 carbon atoms; and h. aryl cyanides containing from 1 to 5 phenyl rings;

i. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, thiocyanide, and isonitrile, and the corresponding acids and salts of said inorganic anions.

32. The method of claim 31 wherein the ligand contains monodentate functional groups selected from the group consisting of: pyridine, 4,4'-bipyridine, ethylenediamine, propylenediamine, 2-aminoethanol, 3-aminopropanol, trimethylamine, triethylamine, tripropylamine, 2-aminopropane, triethanolamine, aniline, 1,4-diaminobenzene, 1,3,5-triaminobenzene, 1,3,5-triazine, imidazole, pyrazine, ethanol, ethylene glycol, 1-propanol, 2-propanol, propylene glycol, n-butanol, sec-butanol, iso-butanol, tert-butanol, 1,4-butanediol, phenol, benzyl alcohol, hydroquinone, 1,3,5-trihydroxybenzene, 1,2,4-trihydroxybenzene, 1,2,3-trihydroxybenzene, thioethane, thiopropane, thiocyclohexane, thiobenzene, 1,4-dithiobenzene, and 1,3,5-trithiobenzene, 1,4-dicyanobenzene, and 1,3,5-tricyanobenzene.

33. The method according to claim 23 in which the reaction mixture containing the microporous material product is heated from 30° C. to 500° C. to partially or completely remove the templating agent.

34. A method for the preparation of microporous materials which comprises the steps of:

Admixing a solution containing one or more metal ions from the group consisting of:

$Mn^{3+}$, $Mn^{2+}$, $Fe^{3+}$, $Fe^{2+}$, $Co^{3+}$, $Co^{2+}$, $Ni^{2+}$, $Ni^+$, $Cu^{2+}$, $Cu^+$, $Ag^+$, $Zn^{2+}$, $Cd^{2+}$; along with the corresponding metal salt counteranion with, one or more ligand substructures being at least one of:

methane, tetraphenylmethane, ethylene, benzene, and adamantane, said ligand substructure having bound thereto carboxylic acid functional groups; in the presence of a templating agent selected from the group consisting of:

a. alkyl amines and their corresponding alkyl ammonium salts, containing linear, branched, or cyclic aliphatic groups, having from 1 to 20 carbon atoms;

b. aryl amines and their corresponding aryl ammonium salts having from 1 to 5 phenyl rings;

c. alkyl phosphonium salts, containing linear, branched, or cyclic aliphatic groups, having from 1 to 20 carbon atoms;

d. aryl phosphonium salts, having from 1 to 5 phenyl rings, e. alkyl organic acids and their corresponding salts, containing linear, branched, or cyclic aliphatic groups, having from 1 to 20 carbon atoms;

f. aryl organic acids and their corresponding salts, having from 1 to 5 phenyl rings;

g. aliphatic alcohols, containings linear, branched, or cyclic aliphatic groups, having from 1 to 20 carbon atoms;

h. aryl alcohols having from 1 to 5 phenyl rings;

i. inorganic anions selected from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of said inorganic anions;

j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylene-chloride, tetrahydrofuran, ethanolamine, triethylamine, and trifluoromethylsulfonic acid.

35. The method of claim 34 wherein the templating agent is pyridine.

36. The method of claim 34 wherein the templating agent is ethanols.

37. The method of claim 34 wherein the ligand is benzene-1,3,5-tricarboxylic acid.

38. The method of claim 34 wherein the ligand is benzene-1,4-dicarboxylic acid.

39. The method of claim 34 wherein the ligand is benzene-1,2,4,5-tetracarboxylic acid.

40. The method of claim 34 wherein the ligand is adamantane-1,3,5,7-tetracarboxylic acid.

41. The method of claim 34 wherein the ligand is 1,1',1'',1'''-methanetetracarboxylic acid.

42. The method of claim 34 wherein the microporous materials are prepared in the presence of a ligand containing one or more monodentate functional groups said ligand selected from the group consisting of:

a. alkyl amines containing at least one alkyl group containing 1 to 10 carbon atoms;
b. aryl amines containing from 1 to 5 phenyl rings;
c. alkyl alcohols containing at least one alkyl group having from 1 to 10 carbon atoms;
d. aryl alcohols containing from 1 to 5 phenyl rings;
e. alkyl thiols containing at least one alkyl group having from 1 to 10 carbon atoms;
f. aryl thiols containing from 1 to 5 phenyl rings;
g. alkyl cyanides containing at least one alkyl group having from 1 to 10 carbon atoms;
h. aryl cyanides containing from 1 to 5 phenyl rings;
i. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, thiocyanide, and isonitrile, and the corresponding acids and salts of said inorganic anions.

43. The method of claim 42 wherein the ligand contains monodentate functional groups selected from the group consisting of: pyridine, 4,4'-bipyridine, ethylenediamine, propylenediamine, 2-aminoethanol, 3-aminopropanol, triethylamine, tripropylamine, 2-aminopropane, triethanolamine, aniline, 1,4-diaminobenzene, 1,3,5-triaminobenzene, imidazole, ethanol, ethylene glycol, 1-propanol, 2-propanol, propylene glycol, n-butanol, tert-butanol, phenol, benzyl alcohol, hydroquinone, 1,3,5-trihydroxybenzene, thioethane, thiopropane, thiobenzene, 1,4-dithiobenzene, and 1,3,5-trithiobenzene, 1,4-dicyanobenzene, and 1,3,5-tricyanobenzene.

44. The method according to claim 34 in which the reaction mixture containing the microporous material product is heated from 30° C. to 500° C. to partially or completely remove the templating agent.

45. A method for the preparation of microporous materials which comprises the steps of:

Admixing a solution containing one or more metal ions from the group consisting of:

$Fe^{3+}$, $Fe^{2+}$, $Co^{3+}$, $Co^{2+}$, $Ni^{2+}$, $Ni^+$, $Zn^{2+}$, along with the corresponding metal salt counteranion with, one or more ligand substructures being at least one of:

benzene and adamantane; said ligand substructure having bound thereto carboxylic acid functional groups; in the presence of a templating agent, selected from the group consisting of:

a. alkyl amines and their corresponding alkyl ammonium salts, containing linear, branched, or cyclic aliphatic groups, having from 1 to 20 carbon atoms;
b. aryl amines and their corresponding aryl ammonium salts having from 1 to 5 phenyl rings;
c. alkyl phosphonium salts, containing linear, branched, or cyclic aliphatic groups, having from 1 to 20 carbon atoms;
d. aryl phosphonium salts, having from 1 to 5 phenyl rings,
e. alkyl organic acids and their corresponding salts, containing linear, branched, or cyclic aliphatic groups, having from 1 to 20 carbon atoms;
f. aryl organic acids and their corresponding salts, having from 1 to 5 phenyl rings;
g. aliphatic alcohols, containings linear, branched, or cyclic aliphatic groups, having from 1 to 20 carbon atoms;
h. aryl alcohols having from 1 to 5 phenyl rings;
i. inorganic anions selected from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of said inorganic anions;
j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, and trifluoromethylsulfonic acid.

46. A method for the preparation of microporous materials which comprises the steps of:

Admixing a solution containing one or more metal ions from the group consisting of:

$Co^{3+}$, $Co^{2+}$, $Ni^{2+}$, $Ni^+$, $Zn^{2+}$, along with the corresponding metal salt counteranion with the benzene ligand substructure;

said ligand substructure having bound thereto carboxylic acid functional groups; in the presence of a templating agent, selected from the group consisting of:

a. alkyl amines and their corresponding alkyl ammonium salts, containing linear, branched, or cyclic aliphatic groups, having from 1 to 20 carbon atoms;
b. aryl amines and their corresponding aryl ammonium salts having from 1 to 5 phenyl rings;
c. alkyl phosphonium salts, containing linear, branched, or cyclic aliphatic groups, having from 1 to 20 carbon atoms;
d. aryl phosphonium salts, having from 1 to 5 phenyl rings,
e. alkyl organic acids and their corresponding salts, containing linear, branched, or cyclic aliphatic groups, having from 1 to 20 carbon atoms;
f. aryl organic acids and their corresponding salts, having from 1 to 5 phenyl rings;
g. aliphatic alcohols, containings linear, branched, or cyclic aliphatic groups, having from 1 to 20 carbon atoms;
h. aryl alcohols having from 1 to 5 phenyl rings;
i. inorganic anions selected from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of said inorganic anions;
j. ammonia, carbon dioxide, methane, oxygen, argon, nitrogen, ethylene, hexane, benzene, toluene, xylene, chlorobenzene, nitrobenzene, naphthalene, thiophene, pyridine, acetone, 1,2-dichloroethane, methylenechloride, tetrahydrofuran, ethanolamine, triethylamine, and trifluoromethylsulfonic acid.

47. The method of claim 46 where the templating agent is pyridine.

48. The method of claim 46 where the templating agent is ethanol.

49. The method of claim 46 wherein the ligand is benzene-1,3,5-tricarboxylic acid.

50. The method of claim 46 wherein the ligand is benzene-1,4-dicarboxylic acid.

51. The method of claim 46 where the ligand is benzene-1,2,4,5-tetracarboxylic acid.

52. The method of claim 46 where the ligand is adamantane-1,3,5,7-tetracarboxylic acid.

53. The method of claim 46 wherein the ligand is 1,1',1",1'''-methanetetracarboxylic acid.

54. The method of claim 46 wherein the ligand contains monodentate functional groups selected from the group consisting of: pyridine, 4,4'-bipyridine, ethylenediamine, propylenediamine, 2-aminoethanol, 3-aminopropanol, triethylamine, triethanolamine, aniline, 1,4-diaminobenzene, imidazole, ethylene glycol, propylene glycol, phenol, hydroquinone, 1,3,5-trihydroxybenzene, thiobenzene, 1,4-dithiobenzene, and 1,3,5-trithiobenzene, 1,4-dicyanobenzene, and 1,3,5-tricyanobenzene.

55. The method of claim 54 wherein the ligand contains monodentate functional groups selected from the group consisting of: pyridine, aniline, 4,4'-bipyridine, 1,4-diaminobenzene, phenol, hydroquinone, ethylenediamine, propylenediamine, 2-aminoethanol, 3-aminopropanol, thiobenzene, 1,4-dithiobenzene, and 1,3,5-trithiobenzene, 1,4-dicyanobenzene, and 1,3,5-tricyanobenzene.

56. The method of claim 54 wherein the ligand contains monodentate functional groups selected from the group consisting of: pyridine, ethylenediamine, propylenediamine, 4,4'-bipyridine, 2-aminoethanol, 3-aminopropanol.

57. The method of claim 46 wherein the ligand has an aryl substructure, and wherein said substructure is all carbon or a mixture of carbon, with an element selected from the group consisting of nitrogen, oxygen, sulfur, boron, phosphorous, silicon and aluminum.

58. The method of claim 46 in which the metal ion is added to the reaction in the form of $Zn(NO_3).6H_2O$, the templating agent is ethanol, the ligand containing multidentate functional groups is benzene-1,3,5-tricarboxylic acid, the ligand containing monodentate functional group is nitrate, and triethylamine and ethanol are cosolvents, and said reaction is carried out in a polyethylene oxide gel at room temperature to give large colorless crystals of $Zn_2(C_9H_3O_6).NO_3(H_2O)_{3.5}(C_2H_5OH)_{0.5}$.

59. The method of claim 46 in which the metal ion is added to the reaction in the form of $Zn(NO_3).6H_2O$, the templating agent is ethanol, the ligand containing multidentate functional groups is benzene-1,3,5-tricarboxylic acid, the ligand containing monodentate functional group is nitrate, and triethylamine and ethanol are cosolvents, and said reaction is carried out at room temperature to give colorless crystals of $Zn_2(C_9H_3O_6).NO_3(H_2O)_{3.5}(C_2H_5OH)_{0.5}$.

60. The method of claim 46 in which the metal ion is added as $Co(NO_3)_2.6H_2O$, the ligand containing multidentate functional groups is benzene-1,3,5-tricarboxylic acid, and pyridine is the ligand containing monodentate functional group and the templating agent, and wherein the reaction is carried out in an ethanol/1,2-dichloroethane solution in the presence of a polyethylene oxide gel to give $CoC_6H_3(COOH_{1/3})_3(NC_5H_5)_2.2/3\ NC_5H_5$.

61. The method of claim 46 in which the metal ion is added as $Co(NO_3)_2.6H_2O$, the ligand containing multidentate functional groups is benzene-1,3,5-tricarboxylic acid, and pyridine is the ligand containing monodentate functional group and the templating agent, and said reaction is carried out in ethanol to give $CoC_6H_3(COOH_{1/3})_3(NC_5H_5)_2.2/3\ NC_5H_5$.

* * * * *

UNITED STATES PATENT AND TRADEMARK OFFICE
CERTIFICATE OF CORRECTION

PATENT NO. : 5,648,508
DATED : July 15, 1997
INVENTOR(S) : Omar M. Yaghi

It is certified that error appears in the above-indentified patent and that said Letters Patent is hereby corrected as shown below:

Column 20, Line 27, Claim 1

"$C^{2+}$, $Rh^{2+}$, $Rh^{+}$"

SHOULD READ

-- $\underline{Co^{2+}}$, $Rh^{2+}$, $Rh^{+}$ --

Column 22, Line 41, Claim 12

"tertiary alkyl mines having"

SHOULD READ

-- tertiary alkyl $\underline{amines}$ having --

Column 23, Line 45, Claim 20

" alkyl thioIs containing"

SHOULD READ

-- alkyl $\underline{thiols}$ containing --

UNITED STATES PATENT AND TRADEMARK OFFICE
CERTIFICATE OF CORRECTION

PATENT NO. : 5,648,508
DATED : July 15, 1997
INVENTOR(S) : Omar M. Yaghi

It is certified that error appears in the above-indentified patent and that said Letters Patent is hereby corrected as shown below:

Column 25, Line 41, Claim 31

"aryl thiols containing"

SHOULD READ

--aryl thiols containing--

Signed and Sealed this

Second Day of December, 1997

Attest:

BRUCE LEHMAN

Attesting Officer

Commissioner of Patents and Trademarks